(12) United States Patent
Godard et al.

(10) Patent No.: US 12,195,726 B2
(45) Date of Patent: Jan. 14, 2025

(54) PRODUCTION OF COLOURED FUNGAL MYCELIUM

(71) Applicant: MUSHLABS GMBH, Hamburg (DE)

(72) Inventors: Thibault Godard, Hamburg (DE); Marian Nassar, Hamburg (DE); Cindy Lau Chin Yee, Hamburg (DE); Wassim W. Ayass, Hamburg (DE)

(73) Assignee: MUSHLABS GMBH (DE)

( * ) Notice: Subject to any disclaimer, the term of this patent is extended or adjusted under 35 U.S.C. 154(b) by 0 days.

(21) Appl. No.: 18/529,535

(22) Filed: Dec. 5, 2023

(65) Prior Publication Data

US 2024/0124833 A1    Apr. 18, 2024

Related U.S. Application Data

(63) Continuation of application No. PCT/EP2023/054646, filed on Feb. 24, 2023.

(51) Int. Cl.
| | |
|---|---|
| *C12N 1/14* | (2006.01) |
| *A23F 3/16* | (2006.01) |
| *A23L 5/43* | (2016.01) |
| *A23L 5/44* | (2016.01) |
| *A23L 31/00* | (2016.01) |

(52) U.S. Cl.
CPC ............... *C12N 1/14* (2013.01); *A23F 3/166* (2013.01); *A23L 5/43* (2016.08); *A23L 5/44* (2016.08); *A23L 31/00* (2016.08)

(58) Field of Classification Search
None
See application file for complete search history.

(56) References Cited

U.S. PATENT DOCUMENTS

| | | |
|---|---|---|
| 3,576,720 A | 4/1971 | Fries et al. |
| 5,846,787 A | 12/1998 | Ladisch et al. |
| 5,879,463 A | 3/1999 | Proenca |
| 8,772,427 B2 | 7/2014 | Hallberg et al. |
| 8,822,657 B2 | 9/2014 | Belanger et al. |
| 9,206,446 B2 | 12/2015 | Lau et al. |
| 9,624,449 B2 | 4/2017 | Howard et al. |

(Continued)

FOREIGN PATENT DOCUMENTS

| | | | | |
|---|---|---|---|---|
| AU | 2010244324 A1 | * | 12/2011 | ........... A23L 1/3002 |
| AU | 2012260431 B2 | * | 3/2016 | ............. A01H 15/00 |

(Continued)

OTHER PUBLICATIONS

Tony Allman Jul. 23, 2020 "The Difference Between Batch, Fed-Batch and Continuous Processes" https://www.infors-ht.com/en/blog/the-difference-between-batch-fed-batch-and-continuous-processes/. (Year: 2020).*

(Continued)

*Primary Examiner* — Felicia C Turner
(74) *Attorney, Agent, or Firm* — LATHROP GPM LLP; James H. Velema, Esq.

(57) ABSTRACT

The present invention relates to a method for the production of a composition comprising a fungal biomass, characterized in that said composition has a particular colour, as well as a composition and a supernatant obtainable according to the method of the present invention, and their use in the production of a food product, in particular a food product characterized by a particular colour.

29 Claims, 14 Drawing Sheets

(56) References Cited

U.S. PATENT DOCUMENTS

| | | | |
|---|---|---|---|
| 2007/0190628 A1* | 8/2007 | Ingledew | C12P 7/08 |
| | | | 435/161 |
| 2017/0362285 A1* | 12/2017 | Liu | C12N 15/80 |
| 2020/0060310 A1 | 2/2020 | Schmidt et al. | |
| 2020/0270559 A1 | 8/2020 | Macur et al. | |
| 2021/0087590 A1 | 3/2021 | Aymard et al. | |
| 2022/0232854 A1* | 7/2022 | Nadal | A23L 31/00 |
| 2024/0108022 A1 | 4/2024 | Godard et al. | |

FOREIGN PATENT DOCUMENTS

| | | | |
|---|---|---|---|
| CA | 3169292 A1 * | 9/2021 | A23J 3/08 |
| CN | 1078872 A | 12/1993 | |
| CN | 101838673 A | 9/2010 | |
| CN | 104276989 A * | 1/2015 | |
| CN | 104446687 A | 3/2015 | |
| CN | 105038298 A * | 11/2015 | |
| CN | 105054261 A | 8/2017 | |
| CN | 107459659 A | 12/2017 | |
| CN | 108203693 A | 6/2018 | |
| CN | 109504613 A | 3/2019 | |
| CN | 212786880 U | 3/2021 | |
| DE | 102014108841 B3 | 5/2015 | |
| DE | 102016110653 A1 | 12/2017 | |
| EP | 2520608 A1 | 11/2012 | |
| EP | 2862890 A1 | 4/2015 | |
| EP | 3366144 A1 | 8/2018 | |
| ES | 2370215 A1 | 12/2011 | |
| GB | 2137226 A | 10/1984 | |
| JP | 2004-081123 A | 3/2004 | |
| KR | 2013-0057507 A | 6/2013 | |
| RU | 2006126544 A | 3/2008 | |
| WO | WO 2002/090527 A1 | 11/2002 | |
| WO | WO 2007/051269 A1 | 5/2007 | |
| WO | WO 2009/007510 A1 | 1/2009 | |
| WO | WO 2009/026923 A2 | 3/2009 | |
| WO | WO 2012/110231 A1 | 8/2012 | |
| WO | WO 2015/134314 A1 | 9/2015 | |
| WO | WO 2015/197048 A1 | 12/2015 | |
| WO | WO 2017/208255 A1 | 12/2017 | |
| WO | WO 2018/114905 A1 | 6/2018 | |
| WO | WO 2018/154095 A1 | 8/2018 | |
| WO | WO 2017/181085 A1 | 10/2018 | |
| WO | WO 2019/046480 A1 | 3/2019 | |
| WO | WO 2021/030412 A1 | 2/2021 | |
| WO | WO 2021/092051 A1 | 5/2021 | |
| WO | WO 2022/136708 A1 | 6/2022 | |

OTHER PUBLICATIONS

Vrabi et al. "Fungal Growth in Batch Culture . . . " Frontiers in Microbiology Oct. 2019 vol. 10 (Year: 2019).*

Yang et al. "A Beginners Guide to Bioprocess Modes . . . " Eppendorf Application Note No. 408 https://www.eppendorf.com/fileadmin/General/Applications/Bioprocess_Landing_Page/Application_408_Fermentation-A-Beginners-Guide.pdf Copyright 2020 pp. 1-16 (Year: 2020).*

Vrabi et al. 2019 "Fungal Growth in Batch Culture" Frontiers in Microbiology vol. 10 pp. 1-11 (Year: 2019).*

Barreto et al. "Modeling Grifola frondosa fungal growth during solid state fermentation" Eng. Life Sci. 2011 vol. 11 No. 3 pp. 316-321 (Year: 2011).*

Balmant et al. 2015 PLOS One A Model for Growth of a Single Fungal Hypha . . . pp. 1-22 (Year: 2015).*

International Search Report and Written Opinion for PCT International Patent Application No. PCT/EP2023/054646, mailed May 3, 2023.

Rybczynska-Tkaczek et al., "Biosorption optimization and equilibrium isotherm of industrial dye compounds in novel strains of microscopic fungi", International Journal of Environmental Science and Technology, Sep. 22, 2016, vol. 13, pp. 2837-2846.

Ahmed et al., "Improvement of Anaerobic Digestion of Lignocellulosic Biomass by Hydrothermal Pretreatment", Applied Sciences, 2019, 9(18): 3853.

Beltrán-García et al., "Lignin degradation products from corn stalks enhance notably the radial growth of basidiomycete mushroom mycelia", Jun. 2001, 45(2): 77-81.

Conrad et al., "Design of an industrial autohydrolysis pretreatment plant for annual lignocellulose", Biomass Conversion and Biorefinery, Jul. 27, 2019, 11: 2293-2310.

Conrad et al., "Two-Step Autohydrolysis Pretreatment: Towards High Selective Full Fractionation of Wheat Straw", Chemie Ingenieur Technik, Sep. 2020, 92(11): 1723-1732.

Extended European Search Report for European Patent Application No. 20217228.4, dated Jun. 11, 2021.

Galappaththi et al., "Nutritional and medicinal benefits of Oyster (Pleurotus) mushrooms: a review", Fungal Biotech, 2021, 1(2): 65-87.

International Search Report and Written Opinion for PCT International Patent Application No. PCT/EP2021/087661, dated Apr. 25, 2022.

International Search Report and Written Opinion for PCT International Patent Application No. PCT/EP2022/071526, dated Nov. 2, 2022.

International Search Report and Written Opinion for PCT International Patent Application No. PCT/EP2022/060150, dated Aug. 19, 2022.

Kim et al., "Development of the Optimal Media for Mycelial Culture of Pleurotus eryngii using the Hot-water Extract of Raw Materials", Korean Journal of Mycology, Apr. 2012, 40(1): 49-53.

Kongo et al., "Cheese: Cehmistry and Microbiology", Encyclopedia of Food and Health, 2016, pp. 735-740.

Papadaki et al., "Upgrading Grape Pomace through *Pleurotus* spp. Cultivation for the Production of Enzymes and Fruiting Bodies", Microorganisms, 2019, 7(7): 207.

Papaspyridi et al., "Optimization of biomass production with enhanced glucan and dietary fibres content by Pleurotus ostreatus ATHUM 4438 under submerged culture", Biochemical Engineering Journal, Jul. 2010, 50(3): 131-138.

Patel et al., "Integrated lignocellulosic biorefinery: Gateway for production of second generation ethanol and value added products", Journal of Bioresources and Bioproducts, May 2021, 6(2): 108-128.

Platt et al., "Increased Degradation of Straw by *Pleurotus ostreatus* sp. 'florida'", European journal of applied microbiology and biotechnology., Jan. 1983, 17: 140-142.

Ruiz et al., "Engineering aspects of hydrothermal pretreatment: From batch to continuous operation, scale-up and pilot reactor under biorefinery concept", Bioresource Technology, Mar. 2020, 299: 122685, ePublished Dec. 25, 2019.

Search Report and Written Opinion for Luxembourg Patent Application No. LU 102852, dated Apr. 5, 2022.

Sidana et al., "Sugarcane Bagasse: A Potential Medium for Fungal Cultures", Chinese Journal of Biology, Mar. 13, 2014, 2014: 1-5.

Wu et al., "Studies on submerged fermentation of Pleurotus tuberregium (Fr.) Singer. Part 2: effect of carbon-to-nitrogen ratio of the culture medium on the content and composition of the mycelial dietary fibre", Food Chemistry, Mar. 1, 2004, 85(1): 101-105.

U.S. Appl. No. 18/285,555, filed Oct. 4, 2023, Thibault Godard, Edible Non-Animal Dairy Substitute Product Comprising Fibrous Mycelium as Protein and Insoluble Fiber Component and Methods of Producing Such.

*U.S. Appl. No. 18/529,535, filed Dec. 5, 2023, Thibault Godard, Production of Coloured Fungal Mycelium.

U.S. Appl. No. 18/255,420, filed Jun. 1, 2023, Thibault Godard, Production of Fungal Biomass.

U.S. Appl. No. 18/285,555 2024/0108022, filed Oct. 4, 2023 Apr. 4, 2024, Thibault Godard, Edible Non-Animal Dairy Substitute Product Comprising Fibrous Mycelium as Protein and Insoluble Fiber Component and Methods of Producing Such.

*U.S. Appl. No. 18/529,535 2024/0124833, filed Dec. 5, 2023 Apr. 18, 2024, Thibault Godard, Production of Coloured Fungal Mycelium.

(56) References Cited

OTHER PUBLICATIONS

U.S. Appl. No. 18/291,918, filed Jan. 24, 2024, Marc Conrad, Process for Continuous Extraction of Lignocellulosic Material.

* cited by examiner

PRODUCTION OF COLOURED FUNGAL MYCELIUM

RELATED APPLICATIONS

This application is a continuation of International Patent Application No. PCT/EP2023/054646, filed Feb. 24, 2023, which claims priority to European Patent Application No. 22158658.9, filed Feb. 24, 2022, the entire disclosures of which are hereby incorporated herein by reference.

FIELD OF THE INVENTION

The present invention relates to a method for the production of a composition comprising a fungal biomass, characterized in that said composition has a particular colour, as well as a composition and a supernatant obtainable according to the method of the present invention, and their use in the production of a food product, in particular a food product characterized by a particular colour.

BACKGROUND OF THE INVENTION

In recent years, the production of food from animals has been receiving attention because of its unsustainability as well as rising concerns about animal welfare. In the context of climate change, many plant-based meat-alternatives have emerged with the aim to reduce $CO_2$ emissions and animal suffering. However, these products are currently produced from three major monocrops (soy, pea, and rice) whose culture requires a lot of land and water, heavily relies on chemical agents (pesticides and fertilizers) and generates a lot of wastes as only protein isolated from these crops is used for producing meat alternatives. In addition, these isolates have a strong bitter taste and no intrinsic texture or intrinsic colouring that would be typical for certain food products, and therefore their use in foods requires further processing steps as well as the addition of further ingredients, including but not limited to flavouring agents, texturizers, and/or colourants. Hence, plant-based alternatives are not necessarily healthy, and their production induces other environmental issues such as deforestation, significant reduction of biodiversity, soil pollution, and/or water contamination.

Production of food using fermentation processes addresses several of these drawbacks. It enables a better use of land as fermenters can be scaled vertically allowing a local food production in cities or villages. Moreover, it requires less water per kilo product than plant protein, and with ongoing development and improvement of filtration and treatment technologies, this water could be recycled in the process. Another advantage of fungal fermentation over the production of conventional plant isolates is comprised within the obtained raw material—fungal biomass—that per nature already has a desired fibrous texture and brings a balanced nutritional profile with complete proteins but also dietary fibres, vitamins and micronutrients providing consumers with a healthy product. In particular, the use of mycelium isolated from the fruiting bodies from known edible mushrooms additionally brings a typical mushroom umami taste specific to this group, varying a bit between the species (e.g., morel, truffle, or button mushroom) and enables the production of clean and tasty products with a very short list of ingredients.

Presently, methods for producing coloured fungal mycelium for use in the production of food products are lacking.

It is noted that fungal mycelium has been previously used for degradation of synthetic dyes and decolourization of industrial effluents.

US 2021/0045410 discloses a method of forming a bound textured substrate comprising: inoculating a textured substrate with at least one mycelium-producing fungi; and growing the mycelium-forming fungi to form a matrix of mycelium inside, outside, or inside and outside of the textured substrate. A specific embodiment is disclosed, wherein adding any combination of colour and flavoring to the textured substrate in such a way that the colour and flavoring or any combination thereof is taken up by the fungi and becomes a part of the mycelium during growth. The present invention differs from US 2021/0045410 in that the mycelium grown according to the present invention is not substrate bound or is bound to powder particles and not to textured substrate.

WO 2021/195175 discloses a certain method for producing a coloured fungal biomass which includes the steps of fermentation and extrusion, wherein the colour is added after extrusion.

U.S. Pat. No. 11,058,137 discloses several examples of food products that has a white or tan colour and teaches in general than the colour can be affected by the substrate components, e.g., plant ingredients that are sometimes combined with the mycelium.

U.S. Pat. No. 11,166,477 discloses a method wherein the myceliated material is mixed with an edible material to yield a food product. In the disclosed method, the edible material may comprise a colourant.

US20090148558 discloses a process wherein a colouring agent can be added to the mycelium in the mixing process.

U.S. Pat. No. 7,035,160 teaches that edible components e.g., colouring agent can be added to an edible (e.g., proteinaceous) substance, suitable for use in a foodstuff, comprising fungal cells of the order Mucorales having a reduced (or low) RNA content. The document further teaches that the colour may depend on the mushroom used.

Wang and Jiu (Water Science and Technology, volume 38, issues 4-5, 1998, pages 233-238) disclose certain aspects of adsorption and degradation of synthetic dyes on the mycelium of *Trametes versicolor*.

Kasinath et al. (Enzyme and Microbial Technology, volume 32, issue 1, 2 Jan. 2003, pages 167-173) disclose certain aspects of decolourization of synthetic dyes by Irpex lacteus in liquid cultures and packed-bed bioreactor.

Chander et al. (Journal of Industrial Microbiology and Biotechnology, Volume 31, Issue 2, 1 Feb. 2004, Pages 94-97) disclose certain aspects of biodecolourisation of some industrial dyes by white-rot fungi.

Document CN113583882 discloses a certain method for preparing fungal mycelium for use in replacement of proteinaceous meat preparation, comprising carrying out liquid mixed fermentation on the edible fungi and the monascus.

Document JPH1075739 discloses a certain method for producing a mineral-containing mushroom mycelium food material, wherein liquid culture of a mushroom mycelium is performed using a medium comprising a food by-product containing a mineral component.

SUMMARY OF THE INVENTION

Desirable are methods of producing the fungal biomass or a composition comprising the fungal biomass characterized in that said biomass or said composition has a particular colour. Particularly desirable are the methods wherein the produced composition is characterized by intense and/or durable colour which is resistant to washing and/or bleaching. Further particularly desirable are methods wherein the degradation of the component that is responsible for the particular colour of the mycelium by said mycelium is avoided.

As apparent to the skilled person, said methods are challenging to implement. The use of mycelium to treat industrial effluents, and thereby e.g., degrade the dyes comprised therein, for example synthetic dyes, is well known in the art. Therefore, one of challenges is to overcome the intrinsic ability of fungal mycelium to degrade a colourant it is exposed to.

Thus, it was an objective technical problem of the present invention to provide improved methods for the production of coloured biomass.

The objective technical problem is solved by the embodiments described herein and as characterized in the claims.

The present inventors have shown that if an additive that gives rise to the colour of the composition is added to the growing (cultured) fungal biomass at a particular time point during its growth/culture or for a particular residence time, the biomass can bind or assimilate said additive in a way that it cannot be easily washed off. The present inventors have further shown that the optimal time point or the optimal residence time may be dependent on the nature of said additive and the desired colour to be achieved.

The invention will be summarized in the following embodiments.

In a first embodiment, the present invention relates to a method for the production of a composition comprising a fungal biomass, characterized in that said composition has a particular colour, the method comprising the steps of:
  (a) providing a growth medium;
  (b) providing at least one fungal strain;
  (c) cultivating the at least one fungal strain in the growth medium;
  (d) supplementing the growth medium with at least one additive that gives rise to the colour of the composition;
  (e) further cultivating the at least one fungal strain in the growth medium supplemented with the at least one additive that gives rise to the colour of the composition;
  (f) harvesting from the growth medium the composition comprising the fungal biomass characterized in that said composition has a particular colour
wherein the particular colour is due to the at least one additive supplemented in step (d).

In a further embodiment, the present invention relates to a composition obtainable according to the method of the present invention.

In again a further embodiment, the present invention relates to a food product comprising the composition obtainable according to the method of the present invention.

In again a further embodiment, the present invention relates to use of the composition obtainable according to the method of the present invention in the production of a food product.

In again a further embodiment, the present invention relates to a supernatant obtainable according to the method of the present invention.

In again a further specific embodiment, the present invention relates to use of the supernatant of the present invention in the production of a food product.

BRIEF DESCRIPTION OF FIGURES

FIG. 2B) Light orange/red coloured mycelium biomass obtained from astaxanthin added after fermentation. Average RGB (228, 182, 133). FIG. 2C) Stereo microscopic image of the orange/red coloured mycelium biomass obtained from astaxanthin added during fermentation.

FIG. 3B) Light brown mycelium biomass obtained from cocoa powder suspension added after fermentation. Average RGB (76, 43, 25). FIG. 3C) Microscopic image of the coloured biomass showing both adsorption and absorption mechanisms. FIG. 3D) Mycelium biomass with cocoa powder added at day 0 (left, colour: light brown—not homogenous) vs in the deceleration phase (right, colour: dark brown—homogenous).

FIG. 4B) Microscopic image of the coloured biomass showing both adsorption and absorption mechanisms.

FIG. 5B: from left to right: (167, 99, 49), (212, 143, 112), (155, 86, 59), (212, 143, 112); FIG. 5C: from left to right: (112, 58, 46), (187, 93, 69), (135, 50, 27), (187, 93, 69).

DETAILED DESCRIPTION OF THE INVENTION

Figure 1:
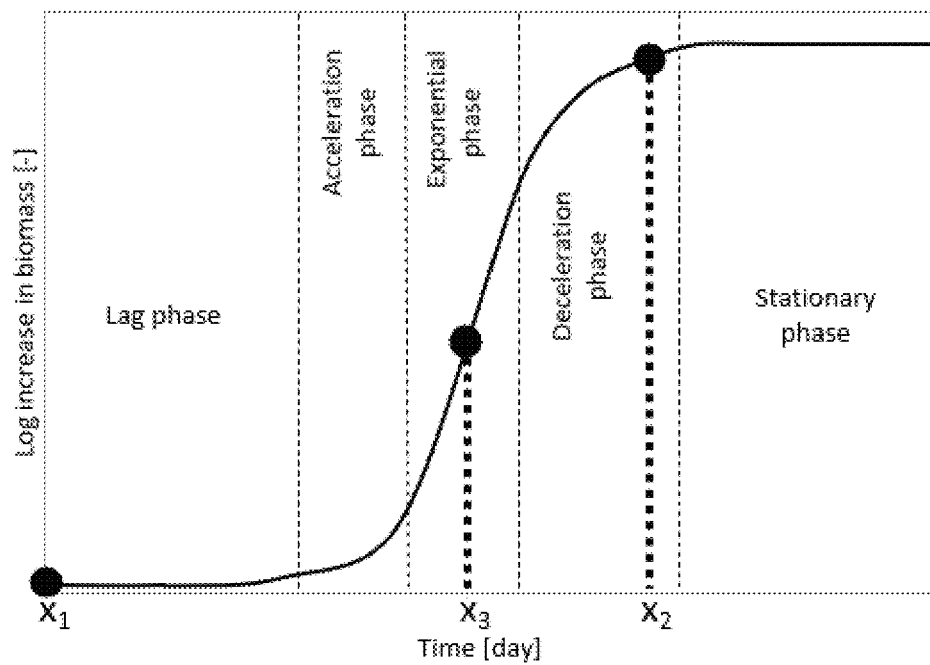
FIG. 1 Typical growth profile of microorganisms where $x_1$ represents time 0 day of the fermentation wherein cocoa and lycopene were added for a batch fermentation, $x_2$ represents the time point in the deceleration phase where astaxanthin and paprika were added for a batch fermentation and $X_3$ represents the time point in the exponential phase where the colourant is added at an optimized concentration for an optimal residence time at steady-state conditions for a fermentation operated in a continuous-mode (biomass, preferably understood as fungal cells, remains in this phase at a constant concentration).

The present invention will be described in the following. It is to be understood that all the combinations of features are envisaged.

In a first embodiment, the present invention relates to a method for the production of a composition comprising a fungal biomass, characterized in that said composition has a particular colour. Having a particular colour as referred to herein is to be understood as property of the material to absorb light of a particular wavelength.

Preferably, the particular colour as referred to herein is a colour that corresponds to that of a particular food product. Several systems for describing colours are known to the skilled person. Particularly useful is using RGB colour classifications, which are based on an additive colour model in which the red, green, and blue primary colours of light are added together in various ways to reproduce a broad array of colours. In said RGB model, each of the component is present preferably at a value of an integer between 0 (i.e., absent) and 255 (i.e., fully present). The typical colours of the common types of food are expressed hereinbelow in the RGB scale.

Red Meats:
  R component between 100 and 255, preferably between 150 and 255
  G component between 0 and 100, preferably between 0 and 60
  B component between 0 and 100, preferably between 0 and 60

White Meats:
  R component between 150 and 255, preferably between 200 and 255
  G component between 100 and 255, preferably between 150 and 255
  B component between 100 and 255, preferably between 150 and 255

Red Fish (Salmon and Tuna):
  R component between 150 and 255, preferably between 200 and 255
  G component between 0 and 200, preferably between 0 and 150
  B component between 0 and 150, preferably between 0 and 100

White Fish:
  R component between 100 and 255, preferably between 150 and 255
  G component between 100 and 255, preferably between 150 and 255
  B component between 100 and 255, preferably between 150 and 255

Cheese:
  R component between 100 and 255, preferably between 150 and 255
  G component between 100 and 255, preferably between 150 and 255
  B component between 0 and 250, preferably between 0 and 200

Yogurts:
  R component between 100 and 255, preferably between 150 and 255
  G component between 50 and 255, preferably between 50 and 200
  B component between 50 and 255, preferably between 100 and 255

Chocolate:
  R component between 0 and 255, preferably between 0 and 200, most preferably 50 and 200
  G component between 0 and 200, preferably between 0 and 150, most preferably 50 and 150
  B component between 0 and 200, preferably between 0 and 150, most preferably 0 and 100

The method for the production of a composition comprising a fungal biomass, characterized in that said composition has a particular colour, comprises the steps of:
(a) providing a growth medium;
(b) providing at least one fungal strain;
(c) cultivating the at least one fungal strain in the growth medium;
(d) supplementing the growth medium with at least one additive that gives rise to the colour of the composition;
(e) further cultivating the at least one fungal strain in the growth medium supplemented with the at least one additive that gives rise to the colour of the composition;
(f) harvesting from the growth medium the composition comprising the fungal biomass characterized in that said composition has a particular colour.

It is to be understood that in the method of the present invention, the particular colour of the composition is due to the at least one additive supplemented in step (d) of said method.

In the first step (a) of the method, the growth medium is provided. Growth of the fungal biomass is known to the skilled person that is capable of choosing a medium that supports the growth of a specific microbe by providing it adequate growth conditions. Accordingly, the medium is not to be particularly limited.

As understood herein, the medium provided in step (a) may further comprise an additive selected from vitamin B12, vitamin B6, vitamin B2, vitamin B3 (also referred to as niacin), riboflavin, thiamine, vitamin A, vitamin E, omega-3 fatty acids, vitamin D2, folic acid, iodized salt (NaCl, further comprising iodine salts in an amount of up to 5% w/w), and minerals (e.g., salts comprising calcium, iron, and/or potassium, etc.). Preferably, the medium as provided in step (a) further comprises vitamin B12 and/or omega-3 fatty acid(s). Said further additives may be added to enhance the nutritional value and taste of potential derived novel food products.

In step (b) of the method of the present invention, at least one fungal strain is provided. Preferably, at least one fungal strain is a single fungal strain, or in other words one fungal strain. However, the term at least one fungal strain may also refer to more than one fungal strain, for example two, three or four fungal strains.

Preferably, the at least one fungal strain is an edible fungal strain. It is preferably understood that an edible fungus is a fungus that can be consumed by a living organism, preferably by a human, providing thereby nutrition and without causing any negative effects to said organism, preferably human.

More preferably, the at least one fungal strain is selected from Basidiomycota and Ascomycota.

Even more preferably, the at least one fungal strain is selected from Pezizomycotina and Agaromycotina.

Even more preferably, the at least one fungal strain is selected from Peziomycetes, Agaricomycetes, and Sordariomycetes.

Even more preferably, the at least one fungal strain is selected from Pezizales, Boletales, Cantharellales, Agaricales, Polyporales, Russulales, Auriculariales, Sordoriales, and Hypocreales.

Even more preferably, the at least one fungal strain is selected from Morchellaceae, Tuberaceae, Pleurotaceae, Agaricaceae, Marasmiaceae, Cantharellaceae, Hydnaceae, Boletaceae, Meripilaceae, Polyporaceae, Strophariaceae, Lyophyllaceae, Tricholomataceae, Omphalotaceae, Physalacriaceae, Schizophyllaceae, Sclerodermataceae, Ganodermataceae, Sparassidaceae, Hericiaceae, Bondarzewiaceae, Cordycipitaceae, Auriculariaceae, Sordoriaceae, Nectriaceae and Fistulinaceae.

Even more preferably, the at least one fungal strain is *P. pulmonarius P. ostreatus, P. citrinopileatus* or *P. salmoneostramineus* or wherein the at least one fungal strain is *M. esculenta, M angusticeps, M. deliciosa,* or *M. rufobrunnea.*

Most preferably, the at least one fungal strain is *P. pulmonarius.*

In one alternative embodiment, the at least one fungal strain selected from Agaricales can be a fungal strain selected from Pleurotaceae. Even more preferably, the at least one fungal strain of the present invention is a fungal strain selected from *Pleurotus pulmonarius, Pleurotus ostreatus, Pleurotus citrinopileatus, Pleurotus florida, Pleurotus eunosmus, Pleurotus columbinus, Pleurotus ferulae, Pleurotus salmoneo-stramineus, Pleurotus Sapidus,* and *Pleurotus salmoneostramineus*, even more preferably selected from *Pleurotus pulmonarius* and *Pleurotus ostreatus,* most preferably *Pleurotus pulmonarius.*

In one alternative embodiment, the fungal strain selected from Morchellaceae is *Morchella esculenta, Morchella angusticeps, Morchella deliciosa, Morchella sceptrifomtis,* *Morchella steppicola, Morchella puncripes, Morchella rufobrunnea, Morchella importuna, Morchella jaurentinaa,* or *Morchella purpumscens*, preferably *Morchella esculenta, Morchella angusticeps* or *Morchella deliciosa.*

It is preferred that the at least one fungal strain is selected from *Pleurotus pulmonarius, Pleurotus florida, Pleurotus citrinopileatus, Pleurotus salmoneostramineus, Morchella esculenta, Morchella angusticeps, Morchella deliciosa,* and *Morchella rufobrunnea.*

Most preferably, the at least one fungal strain is selected from *Pleurotus pulmonarius* and *Morchella rufobrunnea.*

As understood herein, when reference is made to a fungal strain by reciting a particular fungal species, any fungal strain belonging to said species would preferably be understood to be encompassed.

In step (c) of the method of the present invention cultivating the at least one fungal strain in the growth medium.

Typically, a constant temperature is maintained throughout the process, which as known to the skilled person may be selected for optimal growth of a particular fungal strain. For example, in the case of *P. ostreatus* the cultivation is preferably performed at a temperature of between 25 and 30° C. Further preferably, the cultivation is performed at a pH of between 3.0 and 8.5. As understood to the skilled person, selection of pH may be dependent on the fungal strain to be cultivated, or on potential contaminating strains to be excluded from growing. Further preferably, the step cultivation is performed for a time of between 12 and 240 hours.

In step (c) of the method of the present invention, preferably the cultivation is performed as submerged fermentation.

Accordingly, submerged fermentation in the method of the present invention can be operated as a batch, a fed-batch or a continuous process. These three main methods of fermentation are known to the skilled person and differ by outflow and inflow of material from/to the fermentation vessel.

The batch processes are characterized by lack of inflow of material into the fermentation vessel. In a batch process, all nutrients are provided at the beginning of the cultivation, without adding any more in the subsequent bioprocess. During the entire bioprocess, no additional nutrients are added except for gases, acids and bases. The bioprocess then lasts until the nutrients are consumed. This strategy is suitable for rapid experiments such as strain characterization or the optimization of nutrient medium. The disadvantage of this convenient method is that the biomass and product yields are limited. Since the carbon source and/or oxygen transfer are usually the limiting factor, the microorganisms are not in the exponential growth phase for a long time. After the end of a bioprocess run in batch mode, only the biomass or medium is harvested and appropriately processed to obtain the desired product. From the bioreactor point of view, the process is repeatedly interrupted by cleaning and sterilization steps, and the biomass is only produced in stages.

In the fed-batch process, substrate, nutrients, and other substances may be added into the fermentation vessel, to extend the possible culture time or increase the yield, among others. The advantage of feeding during cultivation is that it allows to achieve higher product quantities overall. Under specific growth conditions, the microorganisms and/or cells constantly double and therefore follow an exponential growth curve. Therefore, in certain embodiments the feed rate may be increased exponentially as well. Generally, the substrate is pumped from the supply bottle into the culture vessel, for example through a silicone tube. The user can either manually set the feed at any time (linear, exponential, pulse-wise), or add nutrients when specific conditions are met, such as when a certain biomass concentration is reached or when a nutrient is depleted. The fed-batch process offers a wide range of control strategies and is also suitable for highly specialized applications. However, it may increase the processing time and potentially leads to inhibition through the accumulation of toxic by-products.

Preferably, in the method of the present invention the submerged fermentation is operated as a continuous process. After a batch growth phase, an equilibrium is established with respect to a particular component (also called steady-state). Under these conditions, as much fresh culture medium is added, as it is removed (chemostat). These bioprocesses are referred to as continuous cultures and are particularly suitable when an excess of nutrients would result in inhibition due to e.g., acid or ethanol build up or excessive heating. After reaching steady-state, it is understood that a continuous-mode is constantly operated in the exponential growth phase, wherein cells are maintained at a constant concentration. Transient state is the state before reaching constant stead-state conditions for continuous-mode and it is in fact similar to the start of a batch-mode operation. Other advantages of this method include reduced product inhibition and an improved space-time yield. When medium is removed, cells are harvested, which is why the inflow and outflow rates must be less than the doubling time of the microorganisms. Alternatively, the cells can be retained in a wide variety of ways (for example, in a spin filter), which is called perfusion. In a continuous process, the space-time yield of the bioreactor can be even further improved compared to that of a fed-batch process. However, the long cultivation period also increases the risk of contamination and long-term changes in the cultures. The three most common types of continuous culture are chemostat (the rate of addition of a single growth-limiting substrate controls cell multiplication), turbidostat (an indirect measurement of cell numbers—turbidity or optical density—which needs an additional sensor but is driven by real-time feedback, controls addition and removal of liquid), and perfusion (this type of continuous bioprocessing mode is based on either retaining the cells in the bioreactor or recycling the cells back to the bioreactor; fresh medium is provided and cell-free supernatant gets removed at the same rate).

In one embodiment of the present invention, in the method of the present invention the submerged fermentation is not operated as a continuous process.

In step (d) of the method for the production of a composition comprising a fungal biomass, characterized in that said composition has a particular colour, of the present invention, the growth medium is supplemented with at least one additive that gives rise to the colour of the composition. Said additive will be described in detail hereinbelow.

According to the present inventors, timing of the supplementing in step (d) with respect to steps (c) and (e) is important for the method for the production of a composition comprising a fungal biomass of the present invention, characterized in that said composition has a particular colour. In particular, according to the present inventors, timing of the supplementing step (d) with respect to steps (c) and (e) is important to the colour that characterizes the composition produced in the method for the production of a composition comprising a fungal biomass of the present invention. Without being bound to theory, the timing is important to avoid e.g., the degradation of the at least one additive that gives rise to the colour of the composition by the mycelium.

Preferably, the supplementing in step (d) is done in the lag phase, in the acceleration phase, in the exponential phase, in the deceleration phase, or in the stationary phase of the biomass growth. Different phases of the growth are known to the skilled person. As shown in FIG. 1, if the amount of biomass, which may be measured as concentration of cells present in the culture or the total mass of mycelium formed in the culture, is plotted as logarithm thereof against the time of the culture, initial phase of very limited observed growth is referred to as a lag phase. It is to be understood that the lag phase encompasses the beginning of the cultivation of the fungal biomass. The lag phase, as shown in FIG. 1, is followed by an acceleration phase. The acceleration phase is followed by an exponential phase, which is presented in the graph of the logarithm of the amount of biomass (which may also be referred to as log increase in biomass) plotted against the time of the culture, as a linear curve. As known to the skilled person, in the exponential phase, the amount of biomass is increasing exponentially. Due to limitations of the culture conditions (for example reaching too high concentrations of the cells or using up of the nutrients available in the medium), the exponential growth rate in the culture cannot be infinitely maintained for a batch fermentation. Therefore, a deceleration phase follows the exponential phase where the growth decelerates due to nutrients depletion, preferably depletion of the carbon source. Accordingly, one exemplary carbon source is glucose. Preferably, the deceleration phase is herein defined as the timepoint wherein at least 80 wt. % of the nutrients (e.g., carbon source, e.g., glucose) is depleted, more preferably wherein at least 90 wt. % of the nutrients (e.g., carbon source, e.g., glucose) is depleted, even more preferably wherein at least 95 wt. % of the nutrients (e.g., carbon source, e.g., glucose) is depleted. The skilled person would be in position to determine whether the deceleration has started based on determining the concentration of the carbon source, in particular of glucose, by taking the samples from the reactor/fermenter/flask and measuring the content of glucose (or any other suitable carbon source at issue), for example by using HPLC-based method. Alternatively to determine whether or not the process is in the deceleration phase, the percentage depletion of another limiting nutrient (e.g., nitrogen source) may also be monitored. For example, such a nutrient may be the nutrient that would be completely consumed first (e.g., nitrogen source). As shown in FIG. 1, a stationary phase wherein the amount of biomass stays constant (in other words, the growth rate is equal to the rate of the dying biomass) follows the deceleration phase.

Preferably, the supplementing in step (d) is done in the deceleration phase or in the exponential phase of the biomass growth. It is to be preferably understood that step (d) is done in the deceleration phase when the growth is done as a batch fermentation. It is to be preferably understood that step (d) is done in the exponential phase when the growth is done as a continuous process.

Even more preferably, the supplementing in step (d) is done in the deceleration phase of the biomass growth (for a batch fermentation). As it is to be understood herein, the supplementing in step (d) at the deceleration phase of the biomass growth could avoid oxidative damage to the additive added in step (d), and thus would allow for not using antioxidant in the fungal culture.

If supplementing in step (d) is done in the deceleration phase of the biomass growth, the at least one additive that gives rise to the colour of the composition is a carotenoid, preferably selected from astaxanthin and lycopene, more preferably astaxanthin.

However, in certain embodiments, the supplementing in step (d) is done at the beginning of the biomass growth or before the biomass growth.

As understood herein, the discussion of the time point of step (d) as hereinabove, preferably applies to an embodiment, wherein the at least one fungal strain is not cultured in a continuous mode.

Additives that give rise to the colour of the composition may be sterilized before said addition. The methods of sterilizing such ingredients, including sterile filtration or sanitization, in particular the methods that avoid the use of heat, are known in the art and can thus be implemented by the skilled person.

As further understood to the skilled person, the at least one additive that gives rise to the colour of the composition can already be added to the growing biomass at the seeding stage, i.e., before the cultivation of step (c), which is preferably to be performed in a large-scale fermented or bioreactor. This is particularly preferred in the case wherein the at least one additive supplemented in step (d) is comprises a powder (which is described hereinbelow).

It is to be understood herein that the particular colour of the composition that is produced in the method of the present invention is due to the at least one additive supplemented in step (d). In other words, if the method of the present invention was to be performed in the absence of addition of the additive, i.e., in the absence of step (d), the composition obtained accordingly would not be characterized by said colour. In other words, if cultivations steps (c) and (e) were to be merged in a single cultivation step, wherein no supplementation of step (d) is performed, the composition would not be characterized by said colour.

Figure 3A:
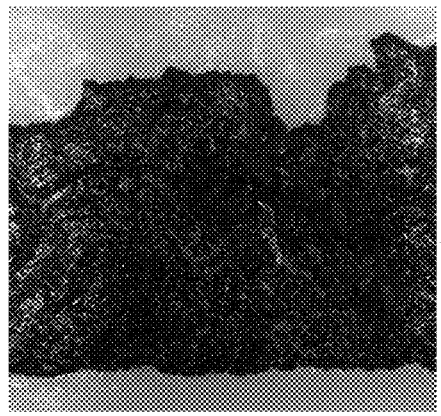
FIGS. 3A-3D FIG. 3A) Dark brown mycelium biomass obtained from cocoa powder suspension added during fermentation. Average RGB (32, 27, 24).
Figure 3B:
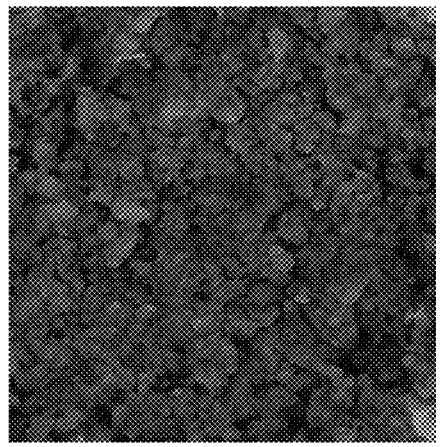
Figure 3C:
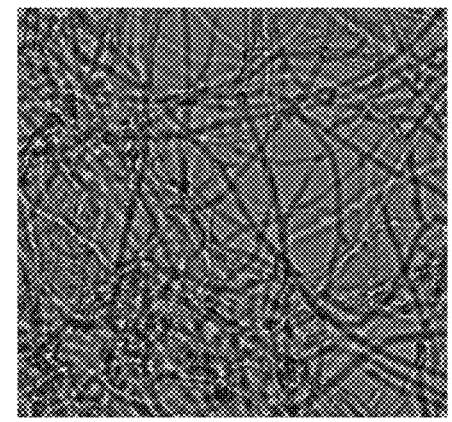
Figure 3D:
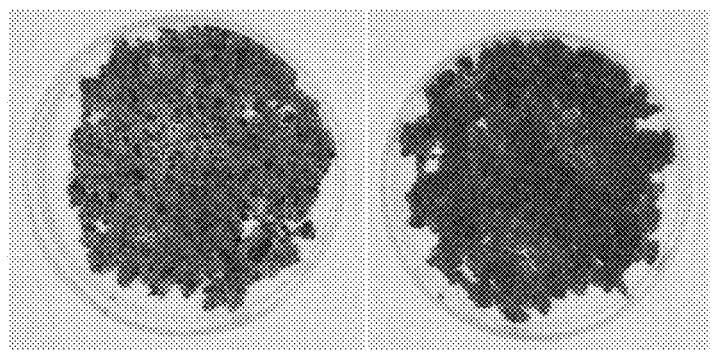

In one embodiment of the present invention, the at least one additive that gives rise to the colour of the composition comprises a material that can form a dispersed phase upon addition to the growth medium. Dispersed phase is herein understood as a system in which particles (e.g., droplets) of one material are dispersed in a continuous phase of another material. Preferably, the at least one additive that gives rise to the colour of the composition comprises a powder or a liquid that can form a dispersed phase upon addition to the growth medium. More preferably, the at least one additive that gives rise to the colour of the composition comprises a powder. As it is to be understood herein, preferably said powder can form a dispersed phase when being supplemented to the growth medium in step (d) or when continuously supplemented at a given concentration in the case of a continuous fermentation process. It is preferably to be understood herein that continuously adding/supplementing said powder allows maintaining its concentration at a desired level during the culture. Additionally, adding powder (e.g., cocoa powder) in the deceleration phase leads to a better homogenous colouration and dispersion compared to adding the colour at day 0. FIG. 3D show the mycelium biomass with cocoa powder added at day 0 (left, colour: light brown—not homogenous) versus an addition in the deceleration phase (right, colour: dark brown—homogenous). As it is to be understood herein, homogeneous colouration and dispersion preferably refers to a situation wherein each of a plurality of samples taken from the biomass would show the same (or substantially the same) colour properties to each other, for example when the colour of each sample is described through an RGB scale, as demonstrated herein. In other words, homogeneous colouration relates to a situation wherein a skilled person when comparing the colour properties of different samples taken from the same biomass reaches the conclusion that these samples have the same colour properties. One can accordingly say that the dispersion of colour is homogeneous. Accordingly, when adding cocoa powder in the deceleration phase, better colour distribution is obtained.

Preferably, the powder is not fully soluble in the growth medium.

Thus preferably, in the method of the present invention for the production of a composition comprising a fungal biomass, characterized in that said composition has a particular colour, the at least one additive that gives rise to the colour of the composition comprises a powder. As preferably understood herein, the powder is a solid in a form of particles, wherein average particle diameter is less than 1000 microns, preferably less than 500 microns, more preferably less than 250 microns. The measurement of particle size distribution can be performed by dynamic light scattering. It is based on the observation that the angle of laser diffracted by a particle corresponds to the size of the particle. In a complex sample containing particles of different sizes, light diffraction results in a specific scattering pattern. By analyzing such pattern, the exact particle size distribution of the sample can be deduced. Herein the diameter of dispersed phase particle refers preferably to a volume median particle diameter, also referred to as d50. Thus, unless otherwise specified, d50 preferably refers to a volume median particle diameter, as measured by DLS. It is noted that a person skilled in the art is capable of determining a volume median particle diameter based on the results of DLS measurement.

Preferably, the powder as discussed herein is selected from a cocoa, a beet powder, a duckweed powder, a spirulina powder, a paprika powder, a turmeric powder, a blueberry powder, a strawberry powder, a berry-based colours powder, a heme powder, a lycopene powder, a betanin powder, an alfalfa powder, a saffron powder, a mint powder, and an annatto extract. As understood herein, a combination of more than one of the powders as recited herein may be used within the scope of the present invention.

As preferably understood herein, cocoa powder relates to a waste cocoa powder, preferably comprising melanoidin.

As preferably understood herein, paprika powder, also referred to as paprika extract, preferably comprises capsanthin and/or capsorubin.

As preferably referred to herein, blueberry powder, also referred to as blueberry extract, comprises anthocyanin.

As preferably referred to herein, beetroot extract, also referred to as beetroot powder, comprises betanin.

As preferably referred to herein, tomato paste, which may also be referred to as lycopene powder, comprises lycopene.

More preferably, the powder is a cocoa powder, a duckweed powder, a spirulina powder, a paprika powder, a turmeric powder, a heme powder or a beet powder, or a combination thereof.

Even more preferably, the powder is a cocoa powder, a paprika powder, or a beet powder.

Most preferably, the powder is a cocoa powder.

It is preferred that the powder as used herein is edible. In other words, it is preferred that the powder can be consumed by a human without causing any adverse effects.

The powder as understood herein may also comprise a lignocellulosic material, in particular a lignocellulosic material originating from industrial and/or agricultural side stream.

Lignocellulosic material is preferably herein defined as a material that comprises dry plant matter. Preferably, said lignocellulosic material comprises cellulose, hemicellulose, and lignin. Preferably, the at least one lignocellulosic material is at least one industrial and/or agricultural side stream, as defined herein. Further preferably, said lignocellulosic material is preferably solid or processed to be a powder before usage. As understood herein, the lignocellulosic material is preferably characterized by a particular colour. Accordingly, the lignocellulosic material is preferably so selected that upon its addition in step (d) of the method of the present invention, the resulting composition is characterized by a particular colour.

Examples of the lignocellulosic material include spent grain, cereal brans, cotton, cotton seed husks, bagasse, cocoa shells, cocoa, cocoa pods, cotton and oil press cakes from sunflower, peanut, hazelnut, palm oil, olive, shells and husks from nuts, grass and leaves waste, wood chips, coffee grounds, coffee husks, coffee silverskin, rapeseed and byproducts from the soy industry like soybean pulp ("okara").

The industrial and/or agricultural side stream as referred to herein is not particularly limited and can be any industrial and/or agricultural side stream known to the skilled person. Preferably, the at least one industrial and/or agricultural side stream refers to one industrial and/or agricultural side stream. Preferably the industrial and/or agricultural side stream is a solid side stream. As defined herein, the term solid side stream relates to any side stream that cannot be handled as a liquid, for example cannot be pumped, as opposed to liquid side streams, for example molasse or vinasse, which can be handled as a liquid and, for example, can flow without application of the mechanical forces. The non-limiting examples of solid side stream are given in the following. Further preferably, the solid side stream is selected from spent grain, cereal brans, cotton, cotton seed husks, bagasse, cocoa shells, cocoa, cocoa pods, cotton and oil press cakes from sunflower, peanut, hazelnut, palm oil, olive, shells and husks from nuts, grass and leaves waste, wood chips, coffee grounds, coffee husks, coffee silverskin, rapeseed and/or byproducts from the soy industry like soybean pulp ("okara"). Even more preferably, the solid side stream is spent grain. The present inventors have surprisingly found that when the growth medium is supplemented with the powder, and wherein said powder is dispersed in the growth medium, the growing mycelium becomes attached during the step (e) to said particles of the powder dispersed in the growth medium. In other words, the growing mycelium traps the particles of the powder dispersed in the growth medium. As a result, the mycelium is present in the growth medium in a form of a composition comprising the mycelium bound to the particles of the powder dispersed in the growth medium. It is to be understood that said particles bound by the mycelium, or trapped by the mycelium, give rise to the colour of the composition obtainable according to the method of the invention.

Examples 2 to 3 show that colour is more intense if the additive being a powder is added during culturing than when the same additive is added once the growth of the fungal biomass is complete.

Thus, preferably, the composition comprising the fungal biomass comprises mycelium bound to the particles of the powder dispersed in the growth medium. It is to be understood that preferably the growing mycelium traps the particles of the powder dispersed in the growth medium. Growing mycelium may also be referred to as active mycelium. In contrast, mycelium that is resting, in other words mycelium at the stationary phase, is less likely to actively trap the particles of the powder.

The present inventors have further experimentally studied the washing-off (i.e., removal upon washing) of said particles from the mycelium that binds them. Preferably, in the composition obtainable according to the method of the present invention, the particles of the powder bound to the mycelium cannot be separated from the mycelium, without disrupting the mycelium culture. Preferably, the separation of the particles of the powder not bound to the mycelium occurs by washing. Further preferably, the particles of the powder bound to the mycelium cannot be separated from the mycelium without disrupting the fungal cells. Thus, without being bound to theory, the present inventors postulate that desirable in the composition of the present invention obtainable according to the method of the present invention is binding of the particles of the powder by the mycelium.

Therefore, preferably, binding of particles by the mycelium refers to them being substantially permanently attached to each other.

The present inventors have surprisingly found that binding of the particles of the powder by the mycelium, in other words trapping of the particles of the powder by the mycelium, occurs preferably during the growth of the mycelium. Thus preferably, in an embodiment of the present invention wherein the at least one additive that gives rise to the colour of the composition comprises a powder, said additive is preferably supplemented to the growth medium during the lag phase for a batch fermentation or said additive is added continuously in a way that their residence time in the fermenter (and preferably also their concentration in the fermenter) enables growth of mycelium bound to the powder particles in the case of continuous process. Even more preferably, in the case of batch fermentation being used, said additive is supplemented to the growth medium substantially at the beginning of the cultivation of the fungal biomass for a batch fermentation.

In other words, preferably, in the method for the production of a composition comprising a fungal biomass, characterized in that said composition has a particular colour step (d) is performed before the commencement of step (c) (preferably for batch fermentation).

According to the present inventors, in an embodiment of the present invention wherein the at least one additive that gives rise to the colour of the composition comprises a powder, wherein said additive is supplemented during the exponential growth phase (for fed-batch operation or continuous operation) or during the deceleration phase or during the stationary phase of the growth for a batch operation, said particles can be washed out of the mycelium to a substantially higher extent than in the case wherein said additive is supplemented during the lag phase or before step (c).

In an embodiment of the present invention wherein the at least one additive that gives rise to the colour of the composition comprises a powder, the composition obtainable in the method of the invention comprises fungal biomass and said powder. Preferably, the particles of the powder bound to the mycelium constitute up to 25% w/w of the composition comprising the fungal biomass, preferably up to 20% w/w of the composition comprising the fungal biomass, more preferably up to 15% w/w of the composition comprising the fungal biomass, even more preferably up to 10% w/w of the composition comprising the fungal biomass. Alternatively, the particles of the powder bound to the mycelium may constitute up to 50% w/w. The amount of the particle bound to the mycelium present in the composition relative to the mycelium, when expressed in w/w % terms, may also be referred to as loading of the mycelium with the powder particles. Preferably, a reference here is made to the particles that are substantially permanently attached to the mycelium. It is to be noted that this amount is dependent on the phase, wherein the powder is added to, which also results in different shades of colouring depending on the concentration present.

In one preferred embodiment, the particles of the powder bound to the mycelium between 20% w/w to 25% w/w of the composition comprising the fungal biomass.

It is further noted that inclusion of powder particles in the composition comprising the fungal biomass of the present invention may be further beneficial to said composition, for example, by improving its nutritional of flavor profile, improving baking properties, or improving properties relevant for applications in cosmetics, pharmaceuticals and/or nutraceuticals.

Thus in other words, the present inventors have demonstrated that the addition of the at least one additive that gives rise to the colour of the composition, said additive being a powder, during the lag phase of the fungal cultivation, leads to increased loading of the mycelium with the powder particles when compared to the addition at different timepoints, e.g., at exponential growth phase or during the deceleration phase.

Preferably, it is to be understood that by controlling the concentration of the colourant, different extents of the colouring of the fungal biomass, i.e., different intensities of the obtained colour, can be obtained. The second factor known to the skilled person to influence the colour intensity is the time of contact between the fungal mycelium and the colourant. It is submitted by the present inventors that preferably one can control the colour intensity by controlling the concentration of the colourant and its contact time with the mycelium. Without being bound by the theory, the present inventors put forward a hypothesis that the accumulation of the colourant in the fungal mycelium may be considered an equilibrium process, as demonstrated in Example 7 and in particular Table 2, showing that regardless of the applied concentration, similar fraction of the colourant has been accumulated with the mycelium.

Accordingly, in one embodiment, in the course of steps (d) and (e) of the method of the present invention preferably at least 50% of the added colourant has been accumulated in the biomass, more preferably, at least 60%, more preferably, at least 70%, more preferably, at least 80%, more preferably, at least 90%. In a preferred embodiment, the fraction of provided colourant that has been accumulated in the biomass is preferably between 60 and 95%, more preferably between 65 and 85%, even more preferably between 70 and 80%. These considerations are particularly applicable if the colourant is Astaxanthin. In other words, preferably the steps (d) and (e) are conducted so that at least 50% of the added colourant is accumulated in the biomass, more preferably, at least 60%, more preferably, at least 70%, more preferably, at least 80%, more preferably, at least 90%, or that that has been accumulated in the biomass is preferably between 60 and 95%, more preferably between 65 and 85%, even more preferably between 70 and 80% of provided colourant is accumulated in the biomass.

In one embodiment of the present invention, the at least one additive that gives rise to the colour of the composition comprises a colourant that is assimilated by the at least one fungal strain.

As preferably understood herein, the colourant is a chemical compound that is characterized by a particular colour. In other words, the colourant is a chemical compound that is characterized by absorption of electromagnetic radiation of a particular wavelength, preferably wherein said wavelength belongs to the visible light spectrum. Thus, said compound appears to have a colour when subjected to visual inspection and exposed to the white light. Certain preferred colourants will be described herein.

The colourant as referred to herein is to be assimilated by the at least one fungal strain. Assimilation of said colourant preferably refers to its uptake into the fungal cell or fungal mycelium. The mechanism of assimilation is not particularly limited and may include passive diffusion into the cells through the cell membrane, active transport of the colourant into the cell by one or more of the cell surface transporters, the mechanism of endocytosis and the like. Preferably, the colourant that has been assimilated is not readily removed from the mycelium by washing the mycelium e.g., with water or water-based solution. It is to be understood that said colourant upon assimilation shall change the colour of the fungal mycelium, or of the fungal biomass, so that the fungal biomass or the composition comprising the same would be characterized by a particular colour.

Thus, the colourant is not particularly limited as long as it can be assimilated by the fungal mycelium and as long as upon assimilation the resulting fungal biomass or the resulting composition comprising the same is characterized by a particular colour.

Preferably, the colourant is a terpene compound. The "terpene compound" may be used interchangeably with the terms "isoprenoid", "isoprenoid compound", "terpene", "terpenoid", and "terpenoid compound" and are known to the skilled person. Terpene compounds comprise, or are composed of, preferably comprise, the so-called ($C_5$) isoprene units. The number of C atoms present in isoprenoids is typically equally divisible by five (e.g., $C_5$, $C_{10}$, $C_{15}$, $C_{20}$, $C_{25}$, $C_{30}$ and $C_{40}$). Irregular epoliterpene isoprenoids have been reported and are also included in the definition of "isoprenoid". Terpene compounds include, but are not limited to, monoterpenes, sesquiterpenes, triterpenes, polyiterpenes, and diterpenes.

Terpene compounds include, but are not limited to, carotene compounds (A) and xanthophyll compounds (B), as shown in the scheme hereinbelow (which is reproduced from Molecules 2020, 25, 1038; doi:10.3390/molecules25051038).

A. Carotenes

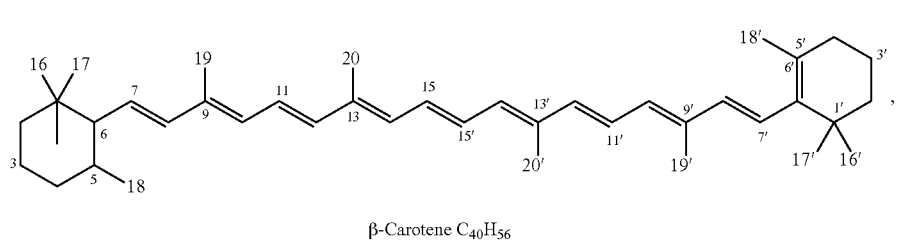

β-Carotene $C_{40}H_{56}$

-continued
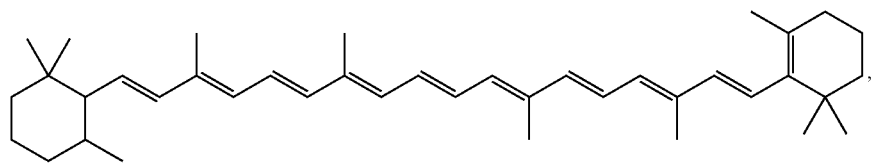
α-Carotene C₄₀H₅₆
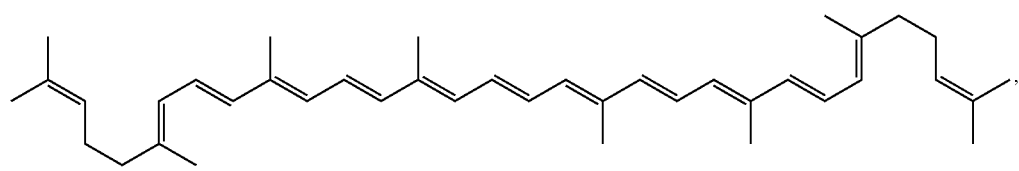
Lycopene C₄₀H₅₆
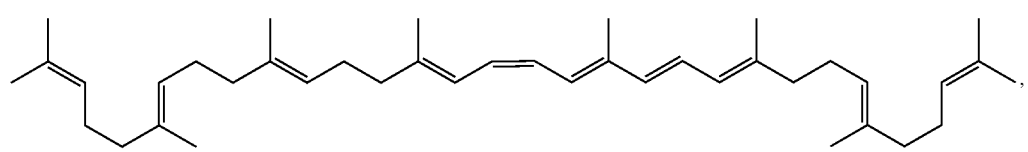
Phytofluene C₄₀H₆₂
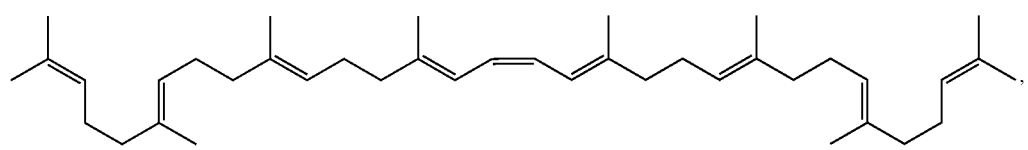
Phytoene C₄₀H₆₂
B. Xanthophylls
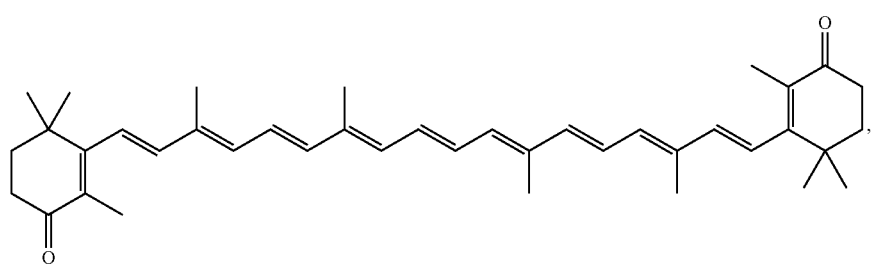
Canthaxanthin C₄₀H₅₆O₂
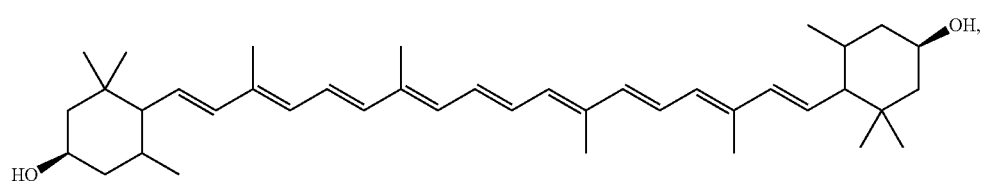
Zeaxanthin C₄₀H₅₆O₂
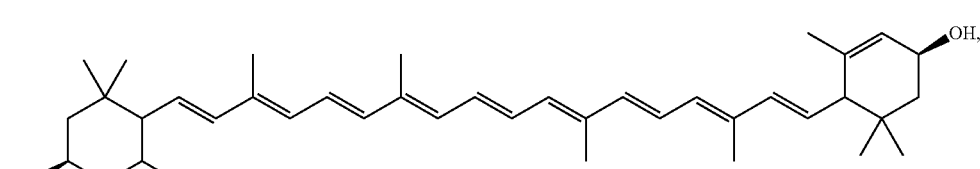
Lutein C₄₀H₅₆O₂

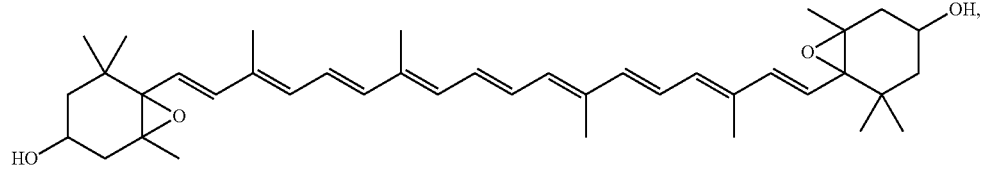
Violaxanthin C₄₀H₅₆O₄
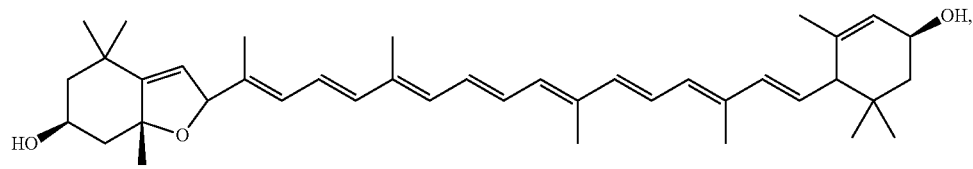
Flavoxanthin C₄₀H₅₆O₃
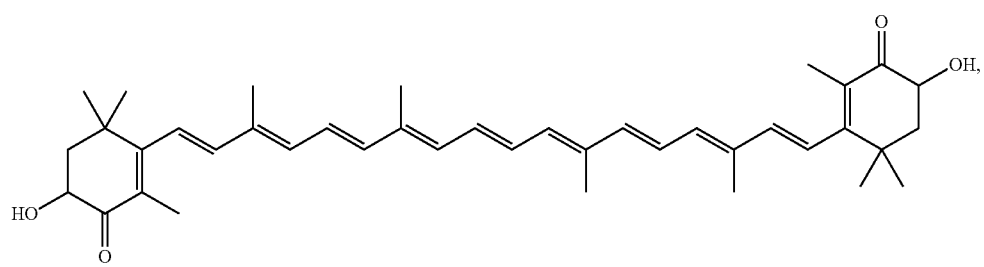
Astaxanthin C₄₀H₅₆O₄
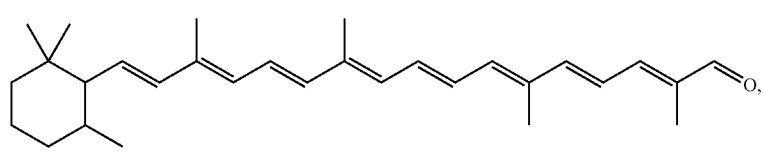
β-Apo-carotenal C₃₀H₄₀O
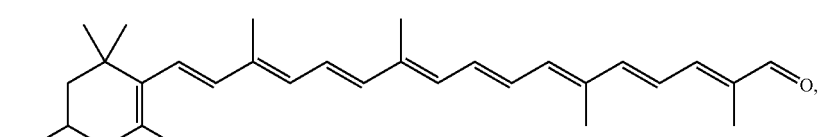
β-Citraurin C₃₀H₄₀O₂
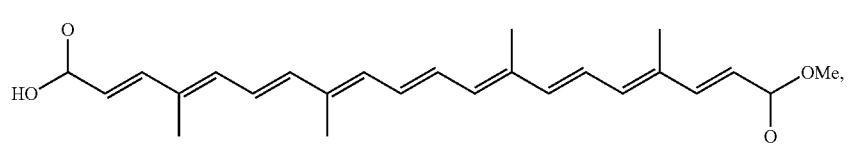
trans-Bixin C₂₅H₃₀O₄
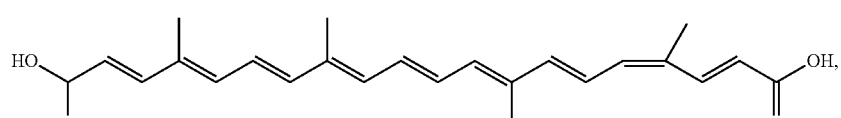
Norbixin C₂₄H₂₆O₄

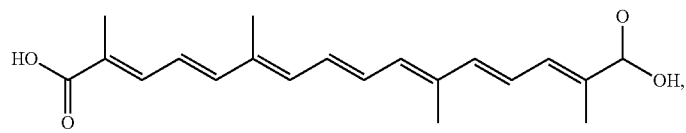

Crocetin C$_{20}$H$_{24}$O$_4$

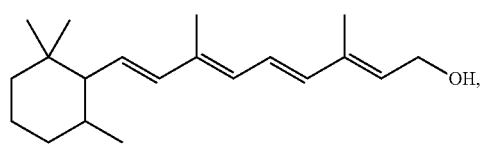

Retinol C$_{20}$H$_{30}$O

Preferably, the terpene compound is a tetraterpene compound, preferably a carotene compound or a derivative thereof, preferably a carotene compound. As understood herein, the derivative of a terpene compound being a colourant is preferably a compound wherein at least 80% atoms, preferably at least 90% atoms remain identical and identically connected as in the parent colourant, and which itself fulfils the definition of a colourant. Non-limiting examples of derivatives are terpene compounds that have been substituted with one or more optional substituents selected from —OH, C$_{1-4}$ alkyl, —COOH, —COO, —COO(C$_{1-4}$ alkyl), O< and =O, preferably selected from OH, C$_{1-4}$ alkyl, —COOH, and —COO(C$_{1-4}$ alkyl). "O<" is herein understood as bivalent oxygen bound to two different carbon atoms, for example an oxygen atom comprised in an epoxide moiety, i.e., a three-membered ring comprising one oxygen and two carbon atoms, or an oxygen atom comprised in a heterocyclic ring, e.g., a five-membered heterocyclic ring. Substitution herein preferably refers to replacement of one or more hydrogen atoms with said optional substituent.

Alkyl as referred to herein is a monovalent radical derived from a saturated hydrocarbon by removal of one of its hydrogen atoms. Alkyl can be linear or branched. Preferably, the term alkyl refers to C$_{1-4}$ alkyl. Particularly preferred alkyl is methyl or ethyl group, more preferably methyl group.

A heterocyclic ring as referred to is preferably a monocyclic ring that is either saturated or partially unsaturated, wherein said ring comprises one or more (such as, e.g., one, two, three, or four) ring heteroatoms independently selected from O, S and N, preferably wherein said ring comprises one O heteroatom, and the remaining ring atoms are carbon atoms. Preferably, said heterocyclic ring is a 3 to 6 membered heterocyclic ring.

Preferably the colourant is selected from carotene terpenes, xhantophyll terpenes, chlorophyll, phycobilins, and anthocyanins. Particularly preferred are carotene terpenes and xhantophyll terpenes.

In one embodiment, the colourant is selected from flavonoid compounds. As understood herein, flavonoid compounds include a 15-carbon atom skeleton, which comprises two phenyl rings and a heterocyclic ring, fused to one of the phenyl rings. Preferred flavonoid compounds include the following backbone:

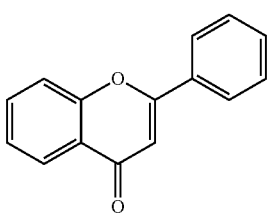 [SMILES: O=c1cc(-c2ccccc2)oc2ccccc12]

In one embodiment, the colourant is selected from fungal pigments, for example carotenoids, melanins, flavins, phenazines, quinones, monascins, violacein, indigo, anthraquinones, naphthaquinones, dihydroxy naphthalene melanin, flavin, monascorubamin, lycopene, ankaflavin, chrysophanol, cynodontin, helminthosporin, tritisporin, erythroglaucin, riboflavin, rubropunctatin; or pigments sourced from microbes such as, *Monascus* sp., *Xanthophyllomyces dendrorhous*, *Penicillium oxalicum*, *Ashbya gossypii*, *Blakeslea trispora*, *Erwinia uredovora*, *Rhodotorula mucilaginosa*, and *Fusarium sporotrichioides*.

The terms pigment and colourant are preferably to be used herein interchangeably.

More preferably, the colourant is astaxanthin or a derivative thereof, more preferably the colourant is astaxanthin.

The present inventors have surprisingly found that the colour that characterizes the composition obtainable according to the method of the present invention in an embodiment of the present invention wherein the at least one additive that gives rise to the colour of the composition comprises a colourant that is assimilated by the at least one fungal strain depends on the timing of supplementing the growth medium with said at least one additive. Without being bound to theory, the terpene compounds are prone to degradation upon assimilation into the mycelium. If the addition of said terpene compound occurs at a cultivation stage where the metabolic activity of the growing mycelium is reduced, i.e., after the exponential growth phase, or preferably during the deceleration phase. The presence of certain reactive functional groups in terpene compounds, e.g., oxygen-comprising functional groups in xanthophylls (i.e., astaxanthin), may increase the propensity of said terpene compounds for being degraded upon assimilation. It is further known to the skilled person that in the presence of oxygen or reactive oxygen species (for example, O$_2$, superoxide radicals, H$_2$O$_2$ or hydroxyl radicals), terpene compounds, e.g., carotene compounds can be oxidized in a process referred to as bleaching. Thus, without being bound to theory, the present inventors note that oxygen availability in the fungal culture during the deceleration phase may be lower than during the phases preceding deceleration, depending on the particular fermentation setup. It is thus conceivable that the assimilation of the colourant by the at least one fungal strain is dependent on the oxygen availability to the at least one fungal strain. Herein the assimilation is understood to involve the processes of assimilation and the process of degradation of said colourant upon assimilation. In the case of a continuous process, the exposure to oxygen or determining effect of oxygen is adjusted by the set residence time in the fermenter. Thus preferably, according to the present invention, the oxygenation or aeration (or the air/oxygen flow, in other words) is controlled in particular in the embodiments wherein the oxygen level may be considered to influence degradation of the colourant/pigment. It is nevertheless preferred that aeration is controlled (and set at a sufficient value, which the skilled person can readily determine) in every process encompassed by the present invention. For example, in one preferred embodiment, the oxygenation rate is set to control the desired dissolved oxygen (DO) level in the medium, referring to the percent of oxygen saturation. Preferably this range is maintained between 10 and 40% v/v.

Without wishing to be bound by theory, the said terpene compounds can also be degraded by the enzymes produced by the mycelium. The most important enzymes catalyzing these redox reactions in this context are: azoreductases, laccases and peroxidases. These enzymes may degrade the terpene compounds.

Thus, as understood herein, the assimilation of the colourant by the at least one fungal strain is dependent on the oxygen availability to the at least one fungal strain. It is to be understood that control of the oxygen supply, in principle known to the skilled person, may be crucial for the method of the invention. It has been demonstrated that the works better in a big scale, using a fermenter with well controlled oxygen supply and/or microenvironment, than in a flask used to evaluate the process at a small scale, because oxygen availability is more controlled in the former case.

The present invention thus provides a method for the production of a composition comprising a fungal biomass of the present invention, wherein the at least one additive that gives rise to the colour of the composition comprises a colourant that is assimilated by the at least one fungal strain, wherein said colourant is so added that its degradation by the mycelium is substantially minimized. As understood herein, by minimizing the degradation of said colourant by the mycelium, a more intense colour of the composition obtainable according to the method of the present invention is obtained. Accordingly, the present inventors have surprisingly found that supplementing of the growth medium with said colourant must occur at a particular phase of the mycelium growth in order to allow for efficient assimilation and avoid degradation. The present inventors have further surprisingly found that upon supplementing the growth medium with said colourant, the culture of the fungal biomass should be performed for a sufficient time to allow for the assimilation, but at the same time the culture duration of the fungal biomass upon addition of said colourant should be minimized in order to avoid degradation of the colourant by the mycelium.

Thus preferably, in the embodiment of the present invention wherein the at least one additive that gives rise to the colour of the composition comprises a colourant that is assimilated by the at least one fungal strain, step (d) is performed once the cultivation in step (c) has reached the deceleration phase (for a batch fermentation). Accordingly, the step (e) is performed afterwards for not more than 72 hours, preferably not more than 48 hours. Furthermore, step (e) is preferably performed for at least 15 mins, preferably for a least 30 mins, even more preferably for at least 1 hour.

Accordingly, the present invention provides a preferred embodiment, wherein the at least one additive that gives rise to the colour of the composition comprises a colourant that is assimilated by the at least one fungal strain, wherein the steps (c) to (e) are as follows:

(c) cultivating the at least one fungal strain in the growth medium until deceleration phase is reached;

(d) supplementing the growth medium with at least one additive that gives rise to the colour of the composition, wherein preferably the at least one additive that gives rise to the colour of the composition comprises a colourant that is assimilated by the at least one fungal strain;

(e) further cultivating the at least one fungal strain in the growth medium supplemented with the at least one additive that gives rise to the colour of the composition preferably for not more than 72 hours, more preferably for not more than 48 hours.

It is envisaged that the method of the present invention may be generalized by the skilled person to a method for producing a composition comprising fungal biomass with a terpene compound assimilated by said biomass. The terpene compound is not to be particularly limited and can for example include cannabis terpenes.

In one embodiment of the present invention, the at least one additive that gives rise to the colour of the composition comprises a coloured microorganism. A coloured microorganism is herein understood as an organism whose cells are characterized by a particular colour, can develop a particular colour under certain conditions, or can secrete a colourant (as defined hereinabove) to the growth medium.

It is to be understood that the coloured microorganism whose cells are characterized by a particular colour or the coloured microorganism that can develop a particular colour under certain conditions (e.g., treatment with an agent, which should not be construed as a limiting example) shall become comprised in the composition comprising fungal biomass obtainable according to the method of the present invention. Thus, its presence in the composition shall confer said particular colour upon said composition.

Alternatively, in the case of a microorganism that can secrete a colourant that can be assimilated by the fungal mycelium, said colourant is expected to be assimilated by the mycelium in course of the step (e) of the method of the present invention.

Preferably, a coloured microorganism is herein understood as an organism whose cells are characterized by a particular colour.

The coloured microorganisms are known to the skilled person. It is understood that microbes can produce a pigment either intracellularly or extracellularly. The added pigment producing microbes can be fungi, bacteria, archaea, algae, or any microbes able to produce pigments. Non-limiting preferred examples of coloured microorganisms are red algae, green algae, brown algae, and cyanobacteria.

Preferred red algae are selected from *Cyanidioschyzon merolae, Atractophora hypnoides, Gelidiella calcicola, Lemanea, Palmaria palmata, Schmitzia hiscockiana, Chondrus crispus, Mastocarpus stellatus, Acrochaetium efflorescens, Audouinella, Polysiphonia ceramiaeformis*, and *Vertebrata simulans*.

Preferred green algae are selected from Caulerpa, Codium, Acetabularia, Cladophora, Trentepohlia and Monostroma.

Preferred cyanobacteria are selected from Chroobacteria, Gloeobacteria, and Hormogoneae, the families Prochloraceae and Prochlorotrichaceae and the genus Foliisarcina, Halospirulina, Phyllonema, Prochlorococcus, Prochloron, Prochlorothrix, Rubidibacter, and Schmidlea.

Preferred brown algae are selected from Phaeophyceae.

Thus, preferably, the coloured microorganism is a microorganism selected from red algae, green algae brown algae and cyanobacteria. For example, the coloured microorganism is a microorganism selected from algae strains such as *Haematoccus pluvialis, Chlorella vulgaris* and cyanobacteria, preferably selected from *Haematoccus pluvialis* and *Chlorella vulgaris*. It is noted that *Haematoccus pluvialis* is known to the skilled person to produce Astaxanthin.

The coloured microorganism according to the invention may also be at least one fungus. Preferably, said coloured fungus comprises *Rhodotorula* fungus, for example *Rhodotorula mucilaginosa*. Using *Rhodotorula* fungus for such purpose is shown in Example 9 and in FIG. 20. Alternatively, said coloured fungus is selected from *Monascus* sp., *Xanthophyllomyces dendrorhous, Penicillium oxalicum, Ashbya gossypii, Blakeslea trispora, Erwinia uredovora, Rhodotorula mucilaginosa*, and *Fusarium sporotrichioides*.

Preferably, *Monascus* sp. added in the decelaration phase to the fungal biomass so that the fungal biomass can be coloured are selected from *Monascus purpureus* (also known as *M. anka* and *M. pilosus*), *Monascus pilosus, Monascus purpureus*, and *Monascus ruber*. Preferably, *Monascus* sp. are added in the form of a powder, such powders are commercially available. Alternatively, *Monascus* sp. culture are grown in a separate tank then said culture added as described hereinabove.

The use of genetically modified coloured microorganisms is also envisaged for the present invention. Thus, in one embodiment, the coloured microorganism is a genetically modified microorganism, for example genetically modified Saccharomyces cerevisiae.

Encompassed by the present invention is also use of $CO_2$-fixing microbes as coloured microorganism.

Figure 21:
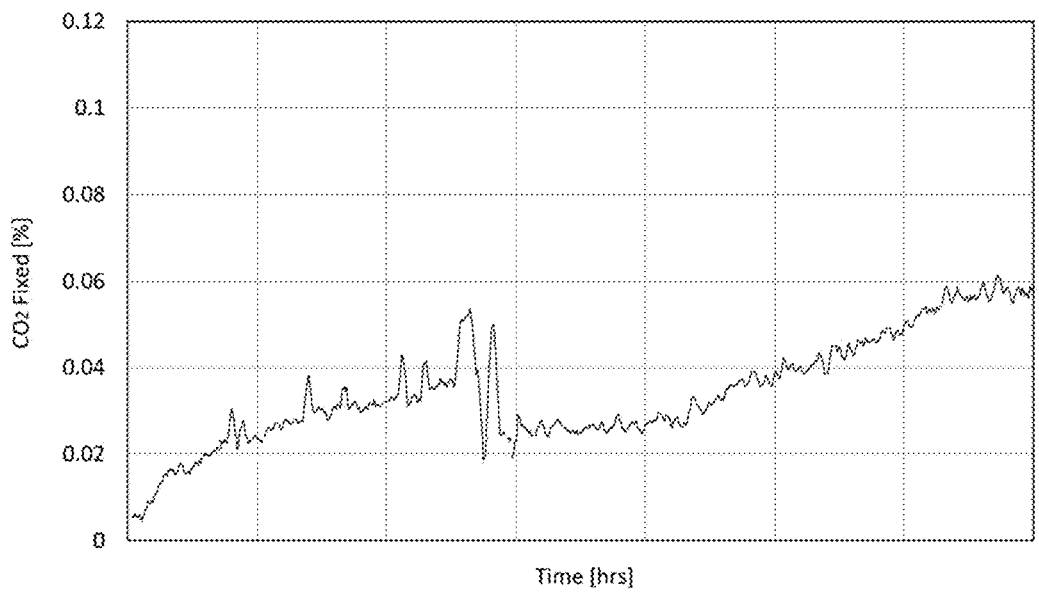
FIG. 21. The trend of the $CO_2$ fixed by the *Haematococcus pluvialis* microalgae.

The use of coloured $CO_2$-fixing microbes to give mycelium its colour will enable an improvement of the carbon footprint of the process as those will feed on the carbon dioxide formed during mycelium growth as well as the modulation of the nutritional profile of the final mycelium products as those microbes can contain nutritious compounds such as omega 3 or vitamin B12 that are otherwise not produced by fungi. To rephrase, the $CO_2$ generated in this case from fungal fermentation is used for the growth of said coloured $CO_2$-fixing microbes (e.g., algae) as discussed in Examples 6 and 10. For example, FIG. 21 shows the trend of the $CO_2$ percentage (by volume) fixed by *Haematococcus pluvialis* green microalgae, which is calculated by subtracting the percentage of the $CO_2$ in the exhaust of the microalgae culture from the percentage of the $CO_2$ input, which is fed from the exhaust of the *Pleurotus pulmonarius* mycelium fermentation. The trend of the $CO_2$ fixed is shown in this figure to be increasing for a time window shown during the microalgae culture. This configuration can for instance be advantageous to use the $CO_2$ produced during fungal fermentation in its normal state or after compression to grow $CO_2$-fixing microbes more efficiently in a separate fermenter before adding them to the fermenter with the at least one fungal strain. Similarly, $CO_2$ captured from other sources can be added to the second fermenter to boost growth of $CO_2$-fixing microbes even further, thus resulting in a carbon neutral or carbon negative process. It is also envisaged to use commercial $CO_2$ as input for the growth of the at least one pigment producing microbes. If required, the fermenter can also be equipped with different light system able to work at different wavelengths (e.g., ultraviolet light, blue-violet light, green light, blue light, red light, etc.) to stimulate the growth of certain type of microbes (e.g., algae) or the production of specific compounds (e.g., vitamin D).

Preferably, the coloured microorganism, as referred to herein, may be co-cultured with the at least one fungal strain of the present invention. This co-culture may be initiated by having both the at least one fungal strain and the coloured microorganism present from the beginning of the co-culturing or by adding the at least one fungal strain once the coloured microorganism had grown to certain extent (i.e., for example, and preferably at the deceleration phase of the growth of the coloured microorganism). Alternatively, the coloured microorganism may be cultured separately from the at least one fungal strain as described herein (for example in a separate reactor) and added to the at least one fungal strain as provided in the present invention (i.e., at the deceleration phase of the fungal strain).

As it is to be understood herein, optionally in all scenarios, more substrates can be added to the culture if further co-fermentation is required. As it is understood by the skilled person, yeast is added in the deceleration phase of the fungus followed by a new substrate addition so that the fungus would still be in the deceleration phase as the yeast would grow faster and consume the added substrate before the fungus. As further apparent to the skilled person, this is the case wherein the coloured microorganism comprising any microbe growing significantly faster than the fungus is used.

By co-culturing the coloured microorganism, preferably a $CO_2$-fixing microorganism, with the at least one fungal strain as provided by the present invention, $CO_2$-fixing organism (which may also be referred to as microorganism or microbe) may use $CO_2$ produced by the at least one fungal strain. This may be the case when the $CO_2$-fixing organism is co-cultured together with the at least one fungal strain, or also when the $CO_2$-fixing microorganism and the at least one fungal strain are cultured in separate reactors, but the $CO_2$ produced by the at least one fungal strain is provided to the $CO_2$-fixing organism, for example by the means of fluid connection between the two reactors. Accordingly, the present invention further relates to an embodiment wherein $CO_2$ produced by the at least one fungal strain is fixed by the coloured microorganism, which herein preferably is a $CO_2$-fixing microorganism. Preferably, the $CO_2$ should be added when enough $CO_2$ has been produced in the fermenter to enable the growth of the $CO_2$ fixing microbe.

It is to be understood that $CO_2$-fixing organism is an organism capable of transforming $CO_2$-fixing into organic compounds in the presence of light, for example selected from cyanobacteria. Preferably, the $CO_2$-fixing organism is selected from the list of coloured microorganism listed herein. In particular, the $CO_2$-fixing organism is selected from cyanobacteria, algae (all types), bacteria, and single-celled organisms (diatoms).

As it is to be understood herein, adding the coloured microorganism after its separate growth may involve either adding the colour extracted from said colured microorganism, excluding the microorganism itself, or as adding the whole culture including the microorganism. Adding the biomass harvested from the culture of the coloured microorganism can also be envisaged as encompassed by the present invention. The microbes could be added while inactive to avoid further co-fermentation, or while active or alive.

Preferably, said coloured microbe is added to the culture of the fungal biomass not before the exponential phase of the growth. This is in particular the case for an embodiment wherein no continuous process is used. Further preferably, it will be understandable to the skilled person that different proportions of the coloured microorganism and fungal biomass may be obtained in the final composition of the present invention, depending on the timing of step (d) and on the supplemented amount (for a batch fermentation), as well as on culturing conditions. It is further noted that the growth of certain coloured microorganisms, e.g., certain algae, require a particular $CO_2$ concentration. Skilled person will be able to adjust the culturing conditions so that desired amounts of the fungal mycelium and of the coloured microorganism are present in the composition. As certain coloured microorganisms may grow faster than fungi, the skilled person would know to take care when supplementing the fungal culture with coloured microorganism (or vice versa) in order to avoid potential overgrowing of the fungal culture with said coloured microorganism. It is noted that continuous culture is not preferred in the case when fungal mycelium is to be co-cultured with coloured microbe, as maintaining the constant composition (i.e., w/w ratio of fungus (i.e., targeted fungal strain(s), or the at least one fungal strain as referred to in step (b) of the method of the present invention) to coloured microorganism (e.g., coloured fungal strain(s)/microbes)) is difficult.

In an embodiment, wherein a continuous culture is used, non-stabilized coloured microbes (no longer active) are induced to grow as fast as the targeted fungal strain(s) (i.e., to limit their growth). Alternatively, for slower coloured microbes, the targeted fungi is induced to grow at the same pace as the coloured microbes (i.e., a growth limitation of the targeted fungi is induced in order for it to grow slower than it actually can).

In a further embodiment, wherein a continuous culture is used, the supplementing in step (d) is done in the exponential phase. Coloured microbes are added continuously to the fermenter at an optimal rate and concentration leading to the target colouring of the biomass after an optimal residence time and pigment concentration are set in the fermenter. The controllable optimal rate of addition ensuring that pigments are not degraded, defines the residence time of the pigments in the fermenter, which is the volume of the fermenter divided by the volumetric flow rate i.e., addition rate of the coloured microbes.

It is preferably understood for a continuous process running at steady-state to be a continuation of a batch process before reaching the exponential phase (i.e., transient state similar to the start of a batch-mode). Therefore, for a continuous process, constantly operating in the exponential phase at steady-state conditions, step (c) is still done under batch operation, step (d) is the addition step of the colourant in the exponential phase, and step (e) reflects the continuous biomass growth with the presence of colourants added continuously at a certain volumetric flow rate, hence dictating the residence time, which is a relevant factor to consider in order to avoid colour degradation and to reach the targeted colour. Step (f) would herein be understood preferably as continuously harvesting the fungal biomass produced in step (e). Step (d) can also (further) comprise continuous supplementing of the at least one additive, parallel with culturing in step (e), so that the concentration of the at least one additive is kept constant during step (e).

In the case of the step (d) being performed before the commencement of step (c), colourants are added directly in transient phase before reaching the continuous phase (i.e., similar to a batch-mode operation).

Encompassed by the present invention is also an embodiment, wherein fungal mycelium or the growth medium comprising the growing fungal mycelium is added to the culture of coloured microorganism. Further encompassed by the present invention is an embodiment, wherein the fungal mycelium and the coloured microorganism are cultured separately, i.e., in separate reactors/fermenters, and mixed together to obtain a composition of the present invention.

In a further embodiment, wherein the coloured microbes added in the order depending on the growing scenarios discussed above, the coloured microbes constitute up to 25% w/w of the composition comprising the fungal biomass, preferably up to 20% w/w of the composition comprising the fungal biomass, more preferably up to 15% w/w of the composition comprising the fungal biomass, even more preferably up to 10% w/w of the composition comprising the fungal biomass. It is to be understood that the coloured microbe preferably should not overgrow the at least one fungal strain as used in the method of the present invention.

Envisaged by the present inventors and encompassed by the present inventors is a possibility of combining different additives that gives rise to the colour of the composition. For example, the growth medium in the method of the present invention could be supplemented with a powder and a soluble colourants. This could happen together (for example with a composition comprising both said powder and said soluble colourant, e.g., a terpene compound), separately (with additional cultivation step in between the two supplementation steps) or sequentially. Optionally, such a growth medium could be additionally supplemented with the at least one coloured microbe and said microbe could be co-cultured with the fungal mycelium.

Encompassed by the present invention is further an embodiment, wherein the at least one additive that gives rise to the colour of the composition that is being supplemented in step (d) of the method of the present invention may comprise an additive selected from vitamin B12, vitamin B6, vitamin B2, vitamin B3 (also referred to as niacin), riboflavin, thiamine, vitamin A, vitamin E, omega-3 fatty acids, vitamin D2, folic acid, iodized salt (NaCl, further comprising iodine salts in an amount of up to 5% w/w), minerals (calcium, iron, potassium, etc.), flavors (salt, pepper, oils, etc.).

Step (e) of the method for the production of a composition comprising a fungal biomass of the present invention, characterized in that said composition has a particular colour, comprises further cultivating the at least one fungal strain in the growth medium supplemented with the at least one additive that gives rise to the colour of the composition. As understood herein, the growth of biomass is continued after the supplementing of step (d) took place. Preferably, cultivation in step (e) is continued for at least 24 hours, at least 48 hours, or at least 72 hours. However, in the case of co-culture with algae, longer periods may be envisaged, for example at least 96 hours or at least 120 hours. Preferably, culturing in step (e) is continued until the growth of the biomass has reached the stationary phase (for a batch fermentation). Preferably, step (e) is to be performed according to the same setup as in step (c).

In step (f) of the method for the production of a composition comprising a fungal biomass of the present invention, characterized in that said composition has a particular colour, the composition comprising the fungal biomass characterized in that said composition has a particular colour is harvested from the growth medium. In other words, the biomass or the composition comprising the biomass is separated from the liquid components of the growth medium.

Harvesting as described herein can be performed according to any methods known to the skilled person, which are not meant to be particularly limited herein.

After the fermentation, the composition comprising the biomass is separated by filtration, centrifugation, or other state-of-the-art techniques, washed with water and concentrated to a concentration suitable for the production of a food product.

In one embodiment, the method of the present invention further comprises the step of recovering a supernatant in step (f).

The supernatant produced during the fermentation as in the method according to the present invention is expected to keep its characteristic colour and thereby can also be used to develop specific health drinks containing antioxidant and a specific aroma, taste and flavours developed during fermentation with edible mushrooms. Mushroom strains are known to produce pleasant volatiles and other compounds with apple or almond taste, for example. They also produce compounds known to regulate the blood sugar level.

It is also envisaged that the supernatant of the present invention could be further processed, e.g., to extract its particular components, e.g., proteins, in particular enzymes produced by microorganism(s) cultured in the medium, polysaccharides, peptides, antioxidants, etc.

The present invention further relates to a composition obtainable according to the method for the production of a composition comprising a fungal biomass of the present invention. Said composition is characterized in that it has a particular colour, particularly a colour selected from the colours characteristic for a food product, as discussed hereinabove. Depending on the additive used in the method of the present invention, said composition may additionally comprise particles of the powder, wherein said particles are bound to the mycelium.

Preferably, the composition of the present invention is characterized in that the composition comprises at least 1 mg of colourant per 100 g of the fungal biomass, preferably at least 5 mg of colourant per 100 g of the fungal biomass, more preferably at least 10 mg of colourant per 100 g of the fungal biomass, even more preferably at least 15 mg of colourant per 100 g of the fungal biomass, even more preferably at least 30 mg of colourant per 100 g of the fungal biomass. It has been demonstrated that the instant composition comprises such amounts of colourant in the exemplary case of colourant being astaxanthin, as shown in Example 8. It is however to be understood that in the case of other colourants, the composition can also comprise more than the values given above per 100 g of the fungal biomass. In the embodiments of the invention wherein the colourant is to be added during the deceleration phase of the growth, one could envisage using lower amounts/concentration of said colourant.

In one further embodiment, the composition of the present invention is characterized in that the composition preferably comprises between 1 and 50 mg of colourant per 100 g of the fungal biomass, preferably between 30 and 40 mg, preferably between 20 and 30 mg of colourant per 100 g of the fungal biomass, more preferably between 10 and 20 mg of colourant per 100 g of the fungal biomass, more preferably between 1 and 10 mg of colourant per 100 g of the fungal biomass. It is preferably understood herein that the numbers recited are referring to a wet biomass, preferably comprising 3 to 30% water.

In one embodiment, the composition of the present invention comprises at least 0.18 wt. % of the colourant (preferably astaxanthin or lycopene), preferably the composition of the present invention comprises at least 0.35 wt. % of said colourant. It is further preferred that the composition of the present invention comprises not more than 5 wt. % of said colourant, more preferably not more than 1 wt. % of said colourant. It is to be understood that wt. %, as referred to herein, preferably refers to the dry weight of said composition. In one exemplary embodiment, the water content of the composition of the present invention is 5-20%, preferably about 10%, more preferably 10%.

It is herein understood that wt. % always refers to a dry weight basis, unless indicated to the contrary, for example unless it is indicated that it is referring to a wet weight basis.

In one further embodiment, the composition of the present invention preferably comprises between 0.01-5 wt. %, preferably 0.1-5 wt. %, more preferably 0.1-2.5 wt. %, even more preferably 0.1-1 wt. %, most preferably 0.1-0.5 wt. % of the colourant. Preferably, the colourant is xanthophyll, carotene or chlorophyll, preferably xanthophyll or carotene. Exemplary xanthophyll and carotene are astaxanthin and lycopene, respectively).

In the composition of the present invention, preferably the at least one additive that gives rise to the colour of the composition is stably bound to the fungal mycelium. In other words, preferably the at least one additive that gives rise to the colour of the composition is irreversibly bound to the fungal mycelium. Example 6 describes the leaching tests of the composition of the invention and demonstrate that no colour is visible on gloves upon contact with the composition. Furthermore, it has been quantitatively shown that none or at most little leaching is taking place as detected by the UV-vis spectroscopy. Accordingly and preferably, "irreversibly bound" may be understood as not amenable, or substantially not amenable to being washed away or removed in other way from the fungal mycelium without altering the structure of said fungal mycelium. Herein, preferably the term "substantially not amenable to being washed away or removed in other way" means that at least 80% of the colourant, preferably at least 90% of the colourant, more preferably at least 95% of the colourant is not amenable to being washed away or removed in other way from the fungal mycelium, without altering the structure of said mycelium. Altering the structure of said mycelium may, in other words, refer to comprising the integrity of the mycelium which leads to release of the colourant, which otherwise is stably bound to it.

Figure 22:
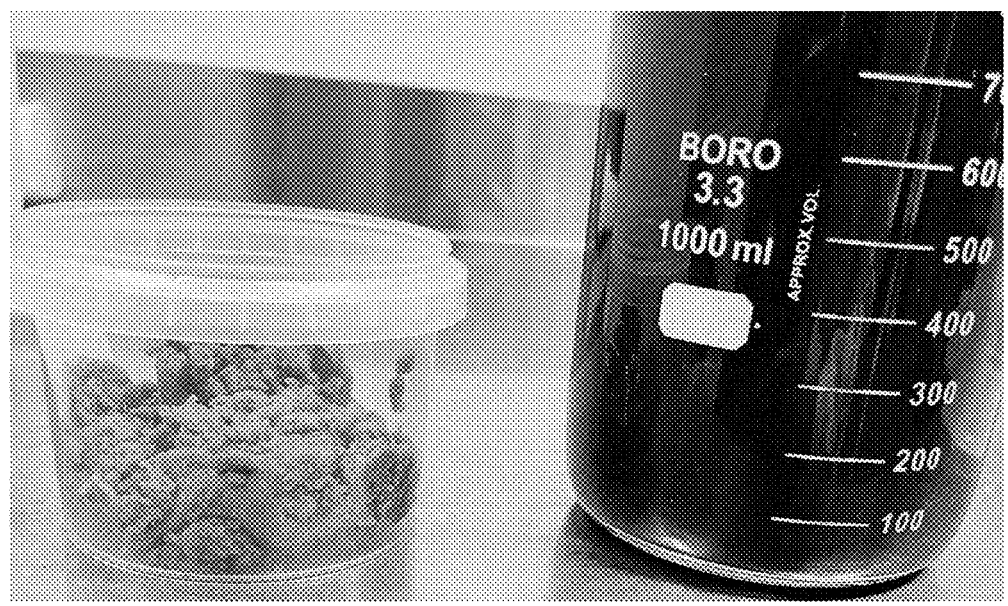
FIG. 22. Mycelium biomass with a light brown colour having an average RGB of (185, 159, 136), coloured with a lignocellulosic extract from wheat bran, said extract has a dark black/brown colour with an average RGB of (23,23, 22). As an illustrative example here, said extract was added at X1.

In one embodiment of the present invention, the at least one additive that gives rise to the colour of the composition comprises an extract of at least one of the lignocellulosic materials listed hereinabove. Preferably, said lignocellulosic material is selected from spent grain, cereal brans, wheat brans, cocoa, and coffee, more preferably from spent grain, cereal brans, wheat brans and cocoa, even more preferably from spent grain, cereal brans and wheat brans, even more preferably spent grain and wheat brans. Preferably, the coloured liquid extracts are added during the fermentation process, at the beginning of the fermentation (X1), or at deceleration phase (X2) (FIG. 1), preferably at deceleration phase (X2) while taking into account the sugar content in the extract so that the fermentation remains in deceleration phase, even more preferably at step (d) as provided in the method of the present invention listed herein to yield a biomass having a homogenous colour and an improved taste. Preferably, the extract has a dark barley colour, or a dark brown//black colour, or a dark brown/red colour which preferably results in the mycelium having a suitable light brown colour to be used in the development of meat analogues (e.g., cooked minced meat). FIG. 22 shows both a mycelium having a light brown colour and a lignocellulosic extract from wheat bran having a dark black/brown coloured solution.

In one further embodiment, the resulting coloured supernatant from a first fermentation which comprised the sugar-rich extract starting at X1, is preferably reused as a colourant for at least one further fermentation, wherein said supernatant colourant is added preferably at the beginning of the next fermentation (X1) or at deceleration phase (X2) of the next fermentation, preferably at deceleration phase (X2) of the next fermentation, even more preferably at step (d) of the next fermentation as provided in the method of the present invention listed herein. Preferably said coloured supernatant comprises at most 20 wt. % sugars and has a similar colour of the extract described herein.

In one further alternative embodiment, said coloured lignocellulosic extracts and/or coloured supernatant are preferably added to the mycelial biomass after its harvesting to colour said mycelial biomass and improve its taste.

Preferably, said extract is prepared according to published methods listed in WO2022136708 disclosing liquid extraction and steam extraction techniques.

Particularly preferred is an extraction process that combines prehydrolysis with steam with extraction/washing step performed with liquid water. Preferably, the lignocellulosic material, preferably the industrial and/or agricultural side stream, is contacted with steam at the temperature of more than 100° C., preferably at the temperature of between 150° C. and 300° C., more preferably at the temperature of between 160° C. and 180° C., even more preferably at the temperature of about 170° C., for a time of up to 20 minutes. Afterwards, the so treated solid is washed with liquid water, preferably at the temperature of 50° C. to 100° C., more preferably at the temperature of 50° C. to 70° C., even more preferably at the temperature of 50° C. to 60° C. Preferably, the washing step as defined herein is performed for the time of between 5 and 60 minutes. Preferably, the liquid extraction comprises extraction of the lignocellulosic material, preferably the industrial and/or agricultural side stream with water at a temperature of between 120 and 220° C., more preferably of between 130 and 200° C. and a pressure of between 1.25 bar and 220 bar, preferably at a pressure of between 2 and 220 bar, more preferably at a pressure of between 6 and 35 bar, even more preferably, a pressure of between 20 and 35 bar. The time is preferably between 5 and 200 minutes, preferably for a time of between 10 and 200 minutes, more preferably for a time of between 10 and 100 minutes.

The composition of the present invention may comprise further enrichments (e.g., additives), for example omega-3 fatty acids, for example sourced from microalgae. In one embodiment, said composition comprises at least an enrichment with said omega-3 fatty acid by an amount of 1, 2.5, 5, 10, 15, 20 wt. %.

The present invention further relates to food product(s) comprising the composition of the present invention.

Preferably, the food product of the present invention comprises at least 10% w/w of the composition of the present invention, preferably at least 20% w/w of the composition of the present invention, more preferably at least 30% w/w of the composition of the present invention, even more preferably at least 35% w/w of the composition of the present invention. It is preferred that the food product of the present invention comprises between 35% w/w to 100% w/w composition of the present invention.

In one embodiment, the mycelium-based or mycelium-containing food product of the present invention comprises between 0.0035 to 5 wt. %, preferably between 0.01 to 5 wt. %, more preferably between 0.01 to 2.5 wt. %, even more preferably between 0.035 wt. % to 0.5 wt. %, even more preferably between 0.05 and 0.35 wt. % of colourant composition of the present invention.

For example, a low concentration of Astaxanthin, preferably not more than 0.9 g/L, leads to a light orange colour, making the resulting coloured biomass suitable to be used in the development of fish analogues or red fish like salmon, caviar or tuna, while a higher concentration of Astaxanthin, preferably more than 0.9 g/L and not more than 1.8 g/L, leads to a red colour, making the resulting coloured biomass suitable to be used in the development of meat analogues or red meats like beef. It is to be understood that by varying concentration of the colourant used in the method of the present invention the colour of the resulting composition may be influenced, and therefore controlled so that the desired colour can be obtained.

As referred to herein, mycelium-based food product preferably comprises at least 90 wt. % of a mycelium composition (i.e., the composition obtainable according to the method of the present invention).

As referred to herein, mycelium-containing food product preferably comprises a mycelium composition in an amount of less than 90 wt. % (i.e., the composition obtainable according to the method of the present invention).

The food product as understood herein may be a dairy product, for example yoghurt, milk drinks and ice cream. The food product as understood herein may also relate to different embodiments of seafood products, for example a crabcake, fishcake, tuna, salmon, or shrimp, as well as to different desserts, including chocolate, brownies, pudding, or cookies.

The present invention is also concerned with the use of a coloured edible fibrous mycelium mass for producing an edible meat substitute product, wherein the edible meat substitute product is preferably selected from products substituting meatballs, sausages, tartar, minced meat, meat spreads, processed meat, Mett meat, foie gras, steak, beef jerky, burger patty, fillet, nugget, salami, whole-cuts, bacon, hot dogs, prosciutto, dried meat and extruded products.

The present invention is also concerned with the use of a coloured edible fibrous mycelium mass for producing an edible dairy substitute product, wherein the edible dairy substitute product is preferably selected from products substituting milk, yoghurt, fresh cheese, whey cheese, cream cheese, medium-hard cheese, hard-cheese, and soft-mould cheese.

The present invention is also concerned with the use of a coloured edible fibrous mycelium mass for producing edible fish analogues or seafood products, for example a crabcake, fishcake, tuna, salmon, or shrimp.

In some embodiments, the meat-analogue or the meat-like food product is understood to preferably have a similar consistency or resemblance or taste to the following animal meat in all its forms (breasts, fillets, thighs, ribs, wings, chunks, steaks, etc.), selected from: beef meat, poultry meat, fish meat, chicken meat, duck meat, goose meat, turkey meat, cow meat, pheasant meat, lamb and mutton meat, white meat, pork meat, ham meat, veal meat, deer or venison meat, seafood meat, prawn meat, crab meat, salmon, cod, pangasius, sardines, mussels and oysters.

In a preferred embodiment, soft meat analogues are preferably meat balls. In another preferred embodiment soft meat analogues are preferably selected from meatballs, sausages, fish fingers, tartar, minced meat, meat spreads, processed meat, Mett meat, luncheon meats, and foie gras.

In another preferred embodiment, non-soft meat analogues are preferably selected from steak, beef jerky, burger patty, fillet, nugget, salami, whole-cuts, bacon, hot dogs, prosciutto, dried meat, and extruded products.

In another embodiment, the concept of non-soft meat and soft meat may be interchangeable, only if ingredients used to produce a traditionally non-soft meat leads to a softer meat-analogue in terms of consistency compared to the traditional definition.

In a preferred embodiment, soft dairy analogues are preferably selected from cream cheese. In another preferred embodiment soft dairy analogues are preferably understood as cream cheese, cheese spreads, processed cheese, whey cheese, pizza cheese, shredded mozzarella cheese, mozzarella cheese, soft cheese, semi-soft cheese, feta cheese, ricotta cheese, cottage cheese, camembert cheese, Roquefort cheese, Gorgonzola cheese, Brie cheese, blue cheese, Buchette cheese, goat cheese, quark, creams, coffee creamer, whipped creme, sour creme, milk chocolate spreads, margarine, butter, desserts, custard. In another embodiment, non-soft or hard dairy analogue are preferably understood as hard cheeses, semi-hard cheeses, cheddar cheese, parmesan cheese, etc.

The food product may be texturized food product or a textured food product. Accordingly, the food product of the present invention comprises all amino acids necessary for human daily intake that cannot be synthetized in novo. Furthermore, the textured food product of the present invention is preferably heat-resistant, boiling resistant and suitable for cooking. For example, the fungal-based food product of the present invention, as described herein, may be a meat replacement product. It is noted that preferably the meat replacement product is a texturized food product or textured food product. It is further noted that the structure of the textured food product improves the acceptability of the textured food product by consumers. It is further noted that intrinsic fibrous texture of the fungal biomass of the present invention maybe beneficial for producing a textured food product or a texturized food product without using conventional texturizing methods such as extrusion.

The food product of the present invention can be further supplemented, for example with preservatives, antioxidants and acidity regulators, thickeners, stabilisers and emulsifiers, pH regulators and anti-caking agents, flavor enhancers, improving agents, stabilizers, thickening agents, colours, and/or glazing agents and sweeteners. Thus, the present invention further relates to the food product, further comprising an additive selected from preservatives, antioxidants and acidity regulators, thickeners, stabilisers and emulsifiers, pH regulators and anti-caking agents, flavor enhancers, improving agents, stabilizers, thickening agents, colours, and/or glazing agents and sweeteners.

Preferably, preservatives include calcium carbonate, acetic acid, potassium acetate, sodium acetate, calcium acetate, lactic acid, sorbates, and malic acid.

Preferably, antioxidants and acidity regulators include ascorbic acid, sodium ascorbate, calcium ascorbate, fatty acid esters of ascorbic acid, tocopherol-rich extract, alpha-tocopherol, gamma-tocopherol, delta-tocopherol, lecithins, sodium lactate, potassium lactate, calcium lactate, citric acid, sodium citrates, potassium citrates, calcium citrates, tartaric acid (L(+))), sodium tartrates, potassium tartrate, sodium potassium tartrate, sodium malate, potassium malate, calcium malates, calcium tartrate, and triammonium citrate.

Preferably, thickeners, stabilisers and emulsifiers (or hydrocolloids) include alginic acid, sodium alginate, potassium alginate, ammonium alginate, calcium alginate, agar, carrageenan, processed euchema seaweed, locust bean gum, guar gum, tragacanth, gum arabic (acacia gum), xanthan gum, tara gum, gellan gum, sorbitol, mannitol, glycerol, konjac, pectins, cellulose, methyl cellulose, ethyl cellulose, hydroxypropyl cellulose, hydroxypropyl methyl cellulose, ethyl methyl cellulose, sodium carboxy methyl cellulose, cellulose gum, enzymatically hydrolysed carboxy methyl cellulose, sodium-potassium and calcium salts of fatty acids, magnesium salts of fatty acids, mono- and diglycerides of fatty acids, acetic acid esters of mono- and diglycerides of fatty acids, lactic acid esters of mono- and diglycerides of fatty acids, citric acid esters of mono- and diglycerides of fatty acids, tartaric acid esters of mono- and diglycerides of fatty acids, microcrystalline cellulose-Cellulose Gel, mono and diacetyl tartaric acid esters of mono- and diglycerides of fatty acids, mixed acetic and tartaric acid esters of mono- and diglycerides of fatty acids, sorbitol and mannitol.

Preferably, pH regulators and anti-caking agents include sodium carbonates, potassium carbonate, ammonium carbonates, magnesium carbonates, hydrochloric acid, potassium chloride, calcium chloride, magnesium chloride, sulphuric acid, sodium sulphates, potassium sulphates, calcium sulphate, sodium hydroxide, potassium hydroxide, calcium hydroxide, ammonium hydroxide, magnesium hydroxide, calcium oxide, magnesium oxide, fatty acids, gluconic acid, glucono delta-lactone, sodium gluconate, potassium gluconate, and calcium gluconate.

Preferably, flavor enhancers include glutamic acid, monosodium glutamate, monopotassium glutamate, calcium diglutamate, monoammonium glutamate, magnesium diglutamate, guanylic acid, disodium guanylate, dipotassium guanylate, calcium guanylate, inosinic acid, disodium inosinate, dipotassium inosinate, calcium inosinate, calcium 5'-ribonucleotides, disodium 5'-ribonucleotides, and glycine and its sodium salt.

Preferably, improving agents include L-cysteine.

Preferably, stabilizers include invertase and polydextrose.

Preferably, thickening agents include polydextrose, oxidized starch, monostarch phosphate, distarch phosphate, phosphate distarch phosphate, acetylated distarch phosphate, acetylated starch. Thickening agents may also include acetylated distarch adipate, hydroxy propyl starch, hydroxy propyl distarch phosphate, starch sodium octenyl succinate, starch-based ingredients, and acetylated oxidized starch. More preferably thickening agents include psyllium husk and/or starch-based ingredients.

Preferably, colours include riboflavins, chlorophylls and chlorophyllins, anthocyanin, betanin, lycopene, copper complexes of chlorophylls and chlorophyllins, terpene compounds such as carotene compounds and xanthophyll compounds, plain caramel, caustic sulphite caramel, ammonia caramel, sulphite ammonia caramel, vegetable carbon, calcium carbonate, iron oxides and hydroxides, curcumin, tartrazine, cellulose gel, cochineal, carminic acid, carmines, azorubine, carmoisine, lutein, a cocoa powder (melanoidin), a beet powder, a tomato extract, a duckweed powder, a spirulina powder, a paprika powder (capsanthin and/or capsorubin), a turmeric powder, a blueberry powder, a strawberry powder, a berry-based colours powder, a heme powder, a lycopene powder, a betanin powder, an alfalfa powder, a saffron powder, a mint powder and an annatto extract. More preferably, colours include riboflavins, chlorophylls and chlorophyllins, copper complexes of chlorophylls and chlorophyllins, plain caramel, caustic sulphite caramel, ammonia caramel, sulphite ammonia caramel, vegetable carbon, calcium carbonate, iron oxides and hydroxides, curcumin, tartrazine, cellulose gel, cochineal, carminic acid, carmines, azorubine, carmoisine, and lutein.

Preferably, glazing agents and sweeteners include isomalt, maltitols, acesulfame potassium, aspartame, cyclamate, saccharin, sucralose, alitame, steviol glycosides, neotame, lactitol, xylitol, and erythritol.

The food product of the present invention can be further supplemented with an additive selected from vitamin B12, vitamin B6, vitamin B2, vitamin B3 (also referred to as niacin), riboflavin, thiamine, vitamin A, vitamin E, omega-3 fatty acids, vitamin D2, folic acid, iodized salt (NaCl, further comprising iodine salts in an amount of up to 5% w/w), minerals (e.g., salts comprising calcium, iron, and/or potassium, etc.), flavors (salt, pepper, oils, herbs and spices), and natural aromatic compounds. As defined herein, herbs and spices include natural aromatic compounds, such as methyl acetate, linalool, limonene, vanillin, etc.

or synthetic ones like aprifloren, cinnamyl propionate, cyclohexadecanolide, and ethyl levulinate.

Preferably, further additives, defined as a compositional ingredient, are selected from vitamin B12, vitamin B6, vitamin B2, vitamin B3 (also referred to as niacin), riboflavin, thiamine, vitamin A, vitamin E, omega-3 fatty acids, vitamin D2, folic acid, iodized salt (NaCl, further comprising iodine salts in an amount of up to 5% w/w), enzymes (e.g., transglutaminase, amylase), minerals (e.g., salts comprising calcium, iron, and/or potassium, etc.), flavors or flavor components (salt, pepper, garlic, onions, mushroom fruiting body pieces, vegetable pieces, ginger, turmeric, curry, sugars (i.e., sucrose, glucose, mono- or disaccharide), oils, lemon juice, orange juice, herbs and spices, yeast flakes), texturized vegetable proteins, and natural aromatic compounds. As defined herein, herbs and spices include natural aromatic compounds, such as methyl acetate, linalool, limonene, vanillin, etc. or synthetic ones like aprifloren, cinnamyl propionate, cyclohexadecanolide, and ethyl levulinate. Such further additives may improve optical visibility, flavour, nutrients, and provide additional texture.

Preferably nutrients are selected from protein rich ingredients (e.g., pea protein isolate, chickpea protein isolate, wheat gluten, egg white powder, and/or mungbean protein isolate), carbohydrate/dietary fiber rich ingredients (e.g., grain-based flours, grain-based starches, legume-based starches, fruit-based fibers, polysaccharides, starch-based ingredients, psyllium husk, inulin, wheat starch, corn starch), vitamins/mineral-rich ingredients, and/or lipid rich ingredients (e.g., all types of edible oils and butters). Fiber-rich ingredients are preferably used to improve freeze thaw stability and/or juiciness.

The composition obtainable according to the method of the present invention is thus useful in the production of a food product of the present invention. Thus, in another aspect, the present invention relates to use of the composition of the present invention in the production of a food product of the present invention.

In a further embodiment, the present invention relates to supernatant that is obtainable by recovery of supernatant in step (f) of the method of the present invention. Said supernatant is useful in the production of a food product. Thus, in a further embodiment, the present invention relates to use of said supernatant in the production of a food product.

The supernatant of the present invention can also be used for the production of beverages, e.g., alcoholic drinks or sweet healthy drinks. It can also be used to produce fermented beverages promoting gut and digestion health and a boosted immunity system. The supernatant could also be dried, and a coloured powder would be obtained. This powder could be used in different fields, especially formulation of cosmetics where there is a rising interest for exopolysaccharides and antioxidants for skin care for instance. One possible application in cosmetics would be an application as moisturizing agent. The supernatant of the present invention can also be used for nutraceutical and/or pharmaceutical applications.

Accordingly and preferably, the supernatant of the present invention preferably does not include mycelium, or substantially does not include mycelium. This supernatant can serve as basis for soft drinks, healthy fermented beverages, or alcoholic drinks. The latter can also be supported by selecting fermentation conditions and production strains in a way that alcohol production is enhanced during the process and increase in the fermentation broth is achieved over time, just as can be observed in typical beer fermentation with brewing yeast. This liquid solution is then further processed to adjust the taste either by adding additional ingredients, known to the skilled person (e.g., sugar, alcohol, acidifying agent, etc.), modifying compounds enzymatically or adjusting the level of alcohol and sugars by methods known by the skilled person (e.g., distillation). Alternatively, depending on the final application, the supernatant preferably contains mycelium, preferably mycelium extracts as mushroom mycelia are known for their ability to produce antioxidants, exopolysaccharides, functional peptides and other metabolites that can be relevant to tackle health aspects such as regulation of blood sugar levels. Hence, the produced drinks can also find application as health drinks in the future.

Preferably, production of functional compounds includes information of compounds produced by the mycelium, such as antioxidants, exopolysaccharides, functional peptides, and other metabolites. Preferably, said functional compounds, which may also be referred to as active compounds, preferably refer to any substance with a beneficial (documented or proven) effect on a biological function, are preferably mycelium-derived active compounds selected from ergothioneine, ergosterol, lovastatin, resveratrol, glutathione, eritadenine, lentinan, and concanavalin A that can be produced in the supernatant. However, this list is not meant to be construed as particularly limited and further compounds produced in the mycelium, as recognized by the skilled person, may also be included. Exemplary compounds originating from *Pleurotus* ostreatus have been recently reviewed (Mishra et al., Int J Biol Macromol, 2021, 182, 1628-1637).

The present invention further relates to a method for producing a beverage, for example a Kombucha, characterized in that a supernatant having at least 0.1 wt. % of filamentous fungi is used.

Preferably, said supernatant used to produce a beverage comprises filamentous fungi in the range of 0.1 to 20 wt. %, more preferably in the range of 1 to 15 wt. %, even more preferably in the range of 1 to 10 wt. %. Alternatively, said supernatant comprises of filamentous fungi in the range of 25 to 80 wt. %, more preferably in the range of 25 to 50 wt. %. It is preferably understood herein that the numbers recited are referring to a wet biomass, preferably comprising 3 to 30% water. For example, if the supernatant comprises 15 wt % of filamentous fungi, it means that 150 g wet biomass is mixed with 850 g supernatant.

The method of the invention preferably comprises the step of transferring functional substances from the mycelium or filamentous fungi cell walls to the supernatant to further enrich it with functional substances. Preferably, said step encompasses a heat treatment under stirring, wherein the supernatant is preferably heated at a temperature ranging between 50 and 150° C., preferably between 85 and 100° C., even more preferably at a temperature about 85° C. for preferably 3 hours at most, more preferably for 2 hours at most, even more preferably for 1 hour at most, under rigorous stirring ranging between 500 and 1500 rpm, more preferably between 500 and 1200 rpm, even more preferably between 500 and 1000 rpm, even more preferably between 700 and 1000 rpm. In other preferred embodiments, the operating temperature is about 120° C. In an alternative embodiment, the heating treatment is preferably performed for at most 30 hours. Alternatively, in the case of fungal autolysis, the temperature of the heat treatment is preferably between 30 and 60° C. It is worth noting that the addition of acid/bases and/or using enzymes like proteases could achieve the same effect of a heat treatment. The addition of acid/bases and/or using enzymes like proteases can also be combined with the heat treatment.

In a preferred embodiment, the mycelium is filtered out completely after enriching the supernatant further with functional substances. Said supernatant is a vital ingredient for the kombucha.

In another preferred embodiment, the mycelium is preferably filtered out after the heat treatment step so that the enriched supernatant so obtained used for the beverage preparation contains not more than 5 wt. % mycelium, preferably not more than 1 wt. %, preferably not more than 0.1 wt. %.

In an alternative embodiment, at most 10 wt. % of mycelium is present throughout the kombucha fermentation process. The mycelium does not only enrich the beverage with functional substances, but also contributes to a better taste. Preferably, the filtered mycelium after the kombucha has a sweet taste suitable for further food applications.

In one further alternative embodiment, the functional substances are preferably extracted via extraction, evaporation and purification techniques known to the skilled person in the art (e.g., ethanol extraction) to yield a powder that can be either added during the kombucha fermentation process or once the kombucha is strained.

Accordingly and preferably, the beverage of the present invention, preferably the kombucha of the present invention, is characterized in that it comprises extracts from mycelium of filamentous fungi. Preferably the content of said extracts in the kombucha final drink is at most 10 wt. %, even more preferably at most 5 wt. %, even more preferably at most 2.5 wt. %, even more preferably at most 1 wt. %, even more preferably at most 0.5 wt. %, even more preferably at most 0.1 wt. %. Preferably said extracts comprises ergothioneine, ergosterol, lovastatin, resveratrol, glutathione, eritadenine, lentinan, concanavalin A, or a combination thereof.

Preferably the resulting supernatant has an Ergothioneine content ranging between 1-1000 mg/L, more preferably between 1-900 mg/L, more preferably between 1-800 mg/L, more preferably between 1-700 mg/L, more preferably between 1-600 mg/L, more preferably between 1-500 mg/L, more preferably between 1-400 mg/L, more preferably between 1-300 mg/L, more preferably between 1-200 mg/L, more preferably between 1-100 mg/L, more preferably between 1-50 mg/L, more preferably between 1-25 mg/L.

In one preferred embodiment, the supernatant has an Ergothioneine content ranging 25 to 1000 mg/L, preferably between 55 and 800 mg/L, more preferably between 80 and 800 mg/L, even more preferably between 350 and 800 mg/L, even more preferably between 400 and 800 mg/L, even more preferably between 400 and 700 mg/L. As it is to be understood herein, ergothioneine value preferably refers to the amount of ergothioneine expressed in mg ergothioneine per L of the supernatant.

For example, depending on the fermentation conditions used, the ergothioneine content in the supernatant after thermal treatment is 1000 mg/L, 800 mg/L, 650 mg/L, 500 mg/L, 350 mg/L, 150 mg/L, 100 mg/L, 50 mg/L, or 25 mg/L using *Pleurotus pulmonarius*; said values are preferably achieved in about 5 to 5.5 days starting X1 (see FIG. 1). The ergothioneine is preferably measured by a high-performance liquid chromatography (HPLC) technique (injection volume of ca. 10 μL; mobile phase preferably comprising 3% acetonitrile and 0.1% acetic acid in water). External calibration with ergothioneine dissolved in water (5 μg·mL−1 to 100 μg·mL−1) is preferably used for quantification. This measurement is preferably performed in a HPLC analyses of ergothioneine were performed on a Prominence system (Shimadzu) equipped with an LC-20AD high-performance liquid chromatography (HPLC) pump, SIL-20AC HT autosampler, SPD-M20A diode array detector (DAD), CBM-20A communication bus module, and LabSolutions Multi LC Data System Manager.

Accordingly and preferably in this scenario, the filamentous fungi is a strain that produces ergothioneine and is selected from Basidiomycota, Ascomycota, Hymenochaetaceae, Agaricomycetes, Sordariomycetes, Tremellomycetes, wherein the preferable species are selected from *Cordyceps* spp., *Inonotus* spp., *Grifola* spp., *Pleurotus* spp., *Ganoderma* spp., *Lentinula* spp., *Tremella* spp., *Trametes* spp., *Lepista* spp., *Tricholoma* spp., *Aspergillus* spp., and/or *Panus* spp.

Alternatively, filamentous fungi include a combination of at least one of the above mentioned ergothioneine-producing fungal strain with a non-ergothioneine producing fungal strain, for example any of the other fungal strains listed in the embodiments described herein.

However, filamentous fungi may also include only a non-ergothioneine fungal strain(s).

According to literature, CN103184246A discloses a preparation method of ergothioneine utilizing a liquid culture of wild *Pleurotus sapidus, Pleurotus pulmonarius* or *Lepisa sordida* to produce ergothioneine with a low yield of 51 mg/L with a cultivation time of 10 days. For example, CN110283856A discloses a method for producing ergothioneine by fermenting the fungal strain *Pleurotus* ostreatus of 3210 with a yield of 300 mg/L, however the process needs at least 25 days between having the mycelium grow on PD for 15 days followed by a fermentation time for 10 days. It was observed in the patent literature that co-fermenting more than one fungal strain can yield to a higher content of ergothioneine (0N112195215 or 0N114214387). And lastly CN109939027A discloses a method for producing ergothioneine by fermenting Hericium erinaceus with glucose and peptone, with a yield of 331 mg/L, however, the production cost of the substrates is high, and the process takes a long time (around 25 days).

An exemplary method of production of such beverage is given in the following.

Method to produce a mycelium-based Kombucha comprises the following:

(1) using the supernatant having at least 0.1 wt. % of filamentous fungi, preferably having filamentous fungi in the range of 0.1 to 20 wt. %, more preferably in the range of 0.1 to 15 wt. %, even more preferably in the range of 0.1 to 10 wt. %. This supernatant is sourced from a fermentation based on at least one fungal strain. Preferably, the supernatant is coloured.

(2) Heating the supernatant at temperature between 70 and 120° C., preferably between 85 and 100° C. and vigorously stirring in the range of 500 to 1000 rpm for a period ranging from 1 to 120 min, preferably from 1 to 60 min, even more preferably from 1 to 30 min.

(3) Adding further sugar, preferably raw cane sugar or food-grade sweeteners, in the range of 5 to 30%.

(4) Mixing the resulting mixture with unpasteurized kombucha SCOBY liquid (Symbiotic Culture of Bacteria and Yeast) so that the ratio between the SCOBY liquid and the supernatant is 1 to 15, preferably 1 to 12, even more preferably 1 to 10 followed by adding 1 solid piece of SCOBY also using the same ratios.

(5) Covering it with a cloth or cheesecloth and keep it in a room between 18° C. and 29° C.

(6) Measuring the sugar content after 1 week with a refractometer and stopping the fermentation when the attained brix score is between 5 to 40° Bx, preferably between 8 and 35° Bx, even more preferably between 10 and 25° Bx with a pH between 4 and 6, preferably between 4 and 5.

(7) Removing or filtering out the SCOBY and the mycelium once the desired properties are reached followed by straining and bottling the Kombucha.

The mycelium may be filtered out before step (4). Brix refractometers are calibrated using the brix scale, where one degree brix (° Bx) is equal to 1% sucrose by mass.

Further additives are preferably added at either at step (3) with the added sugars to further flavour the drink or at step (7) to further dilute the Kombucha with the additives. Preferably such additives are selected from any tea sort (e.g., green tea, white tea, black tea, fruit tea, herbal tea, or a combination thereof), syrups, aloe vera, coffee, fruit juices, vegetable juices, ginger extract, herbs/spices, dried fruits, and fruit/nuts extracts.

It is understood herein that the functional compounds of interest here i.e., in the scenario of producing a healthy drink, are the ones present in the supernatant and not the in the mycelium. The presence of mycelium in the supernatant is used to enrich the supernatant with more extracts before fermenting it further to a healthy drink (e.g., kombucha).

The present invention further relates to a beverage, preferably a kombucha, characterized in that it is obtainable according to the method of the present invention, and originates from supernatant comprising fungal mycelium, as described hereinabove. Accordingly and preferably, the beverage of the present invention, preferably the kombucha of the present invention, is characterized in that it comprises extracts from mycelium of filamentous fungi. Preferably, the mycelium of filamentous fungi originates from fungal species producing ergothioneine. Accordingly and preferably, the beverage of the present invention (the kombucha of the present invention) comprises ergothioneine.

It is understood that the final food product based on the disclosed composition may include the supernatant obtainable in the process of the production of composition of the present invention. Accordingly, the final fungal-derived food product based on the disclosed composition may be said supernatant itself, or the coloured biomass or a combination thereof or any related extracts from each individual product or a combination thereof. Therefore, the disclosed composition may be applicable to at least one form of these products, as it would be apparent to the skilled person.

In a further embodiment, the present invention relates to use of the composition of the present invention or the supernatant of the present invention in the production of cosmetics, pharmaceuticals, or nutraceuticals.

Accordingly, in one embodiment, the present invention relates to a cosmetic comprising the composition of the present invention and/or the supernatant of the present invention. In a further embodiment, the present invention relates to a pharmaceutical comprising the composition of the present invention and/or the supernatant of the present invention. In again a further embodiment, the present invention relates to a nutraceutical comprising the composition of the present invention and/or the supernatant of the present invention.

In one embodiment of the present invention, the composition of the present invention is used in the production of the composite materials, said materials comprising the fungal mycelium. It is to be understood that said composite material would be characterized by a particular colour, originating from the composition comprising the biomass of the present invention. Preferably, the at least one additive supplemented in step (d) of the method of the present invention is selected from phthalocyanine blue, phthalocyanine green, diarylide pigments, quinacridone, alizarin, pyrroles, and natural gilsonite.

The invention is illustrated by the following examples, which however are not to be construed as limiting. In all the below examples, the mycelium to be coloured is based on *P. pulmonarius*, if not otherwise indicated.

EXAMPLES

The average RGB scale was measured with a PCE-RGB colourimeter (DIN 5033). This was a beneficial methodology to quantify the different shades of colours (light vs. dark) with averaged measurable values. However, in some cases, the colour difference was obvious to be assessed and recognized by the naked eye.

Example 1. Astaxanthin as a Colourant

Astaxanthin powder (5 wt. % concentrated) extracted from microalgae *Hematococcus pluvarius* was used for colouring of mycelium biomass. A 10 g/L concentrated stock solution of the powder was prepared and autoclaved for 15 min at 121° C. At day 5 of the fermentation i.e., during the deceleration phase, the flask was taken out of the incubator and placed under the clean bench. 5 mL of the autoclaved astaxanthin solution (equivalent to 0.9 g/L or 0.09 wt. % of astaxanthin as final concentration) was added to the fermentation culture and the flask was returned to the incubator to resume fermentation. On day 6, the fermentation was stopped, and the flask was harvested and drained with a cheesecloth. Orange/red mycelium biomass was obtained.

The same experiment was parallelly performed with the same time frames, but without the addition of a colourant in order to replicate the colouring procedure mentioned above but after fermentation. On day 6 of this fermentation (equivalent to day 5 with respect to the first scenario), the biomass was harvested and drained with a cheesecloth. The biomass was then soaked in a solution of 0.9 g/L of astaxanthin prepared in 0.9 wt. % NaCl solution for 1 day at ambient temperature to have the biomass exposed to the colour for 1 day in both scenarios. In this case, the biomass was slightly coloured.

Figure 2A:
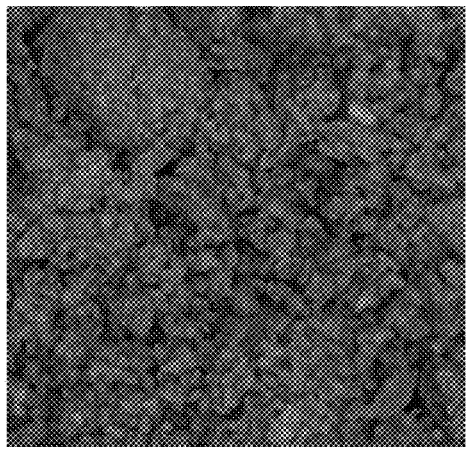
FIGS. 2A-2C FIG. 2A) Orange/red coloured mycelium biomass obtained from astaxanthin solution added during fermentation. Average RGB (186, 70, 43).
Figure 2B:
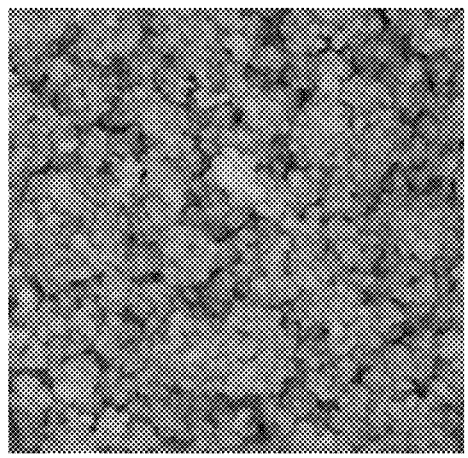
Figure 2C:
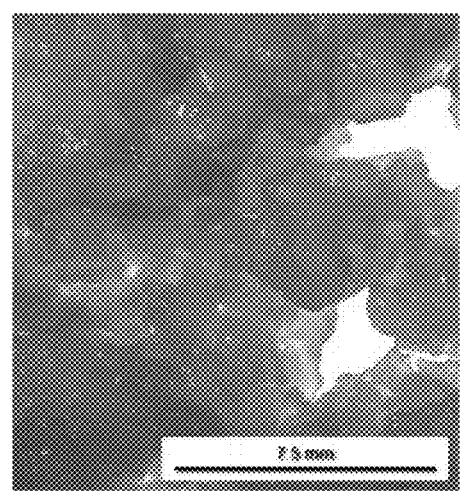

The panels of FIG. 2 show a comparison of the coloured biomass in both scenarios. The mycelium biomass obtained from colouring during fermentation (FIG. 2A) is more prominent and intense (also fits better to the RGB values for red meats) when compared to the one obtained from colouring after fermentation using the same concentration of astaxanthin solution (fits better to the RGB values for white meats) (FIG. 2B). Additionally, adding astaxanthin at the beginning of the fermentation i.e., in the lag phase, resulted in this dye decomposing, which indicates the importance of the time of addition that is dictated by the chemical nature of the colourant.

Example 2. Cocoa as a Colourant

Cocoa powder was used for colouring the mycelium biomass. 100 g/L concentrated stock suspension was prepared and autoclaved for 15 min at 121° C. 10 mL of the autoclaved cocoa suspension (concentration of 20 g/L of cocoa suspension i.e., 2 wt. %) was added at t=0 min of the fermentation in one flask, while running in parallel a control flask without adding any cocoa. Both flasks were inoculated from an agar plate and placed in an Innova 44 incubator for 6 days. On day 6, both flasks with and without cocoa were harvested by two centrifugation steps. Fermentation broths from both flasks were transferred to 50 mL falcons and centrifuged with a speed of 5000 rpm at 4° C. for 20 min. After the first centrifugation, the supernatant was discarded, and the biomass was resuspended in tap water for washing. Both falcons were added again to the centrifuge at the same conditions. Subsequently, the washing water was discarded to isolate the washed biomass. The biomass harvested from the flask with cocoa showed dark brown/black mycelium biomass, while the other biomass was neutral in colour (yellowish white). This neutral biomass was soaked in 20 g/L cocoa suspension (same concentration as above) for 6 days to replicate the fermentation duration performed above. The results show that the biomass coloured after fermentation has a lighter colour compared to the dark coloured biomass obtained when this type of colourant is present throughout the whole fermentation process (FIGS. 3A and 3B). When cocoa encounters the "active mycelium" i.e., mycelium that is actively growing, the resulting colour is darker due to more active trapping of particles along with particles diffusing into the mycelial structure, versus the case where "resting mycelium" i.e., mycelium that is dormant at the stationary phase would only be coloured due to particles diffusing into the mycelial structure leading to a lighter colour. Additionally, it has been shown that adding cocoa powder in the deceleration phase leads to a better homogenous colouration compared to adding the colour at day 0. FIG. 3D show the mycelium biomass with 3 g/L cocoa powder added at day 0 (left, colour: light brown—not homogenous) versus an addition in the deceleration phase (right, colour: dark brown—homogenous).

Example 3. Paprika as a Colourant

Figure 4A:
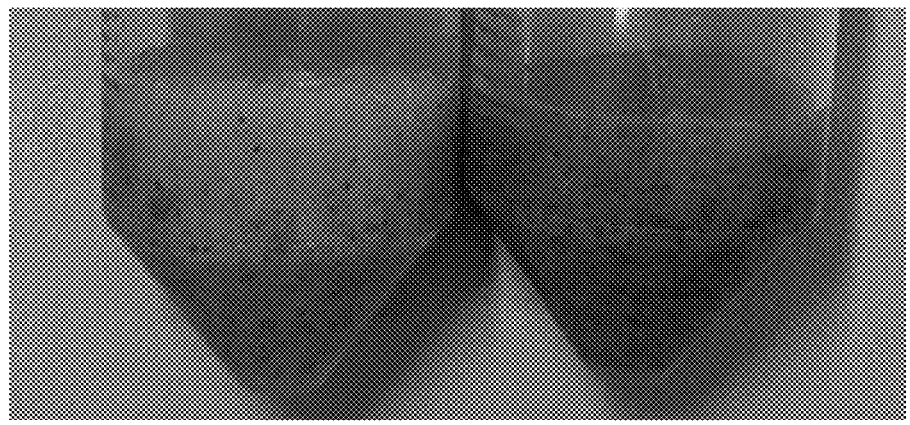
FIGS. 4A-4B FIG. 4A) Light orange (left) and dark orange (right) coloured mycelium biomass obtained from paprika suspension added during fermentation. Average RGB: left (151, 99, 59), right (119, 55, 33).
Figure 4B:
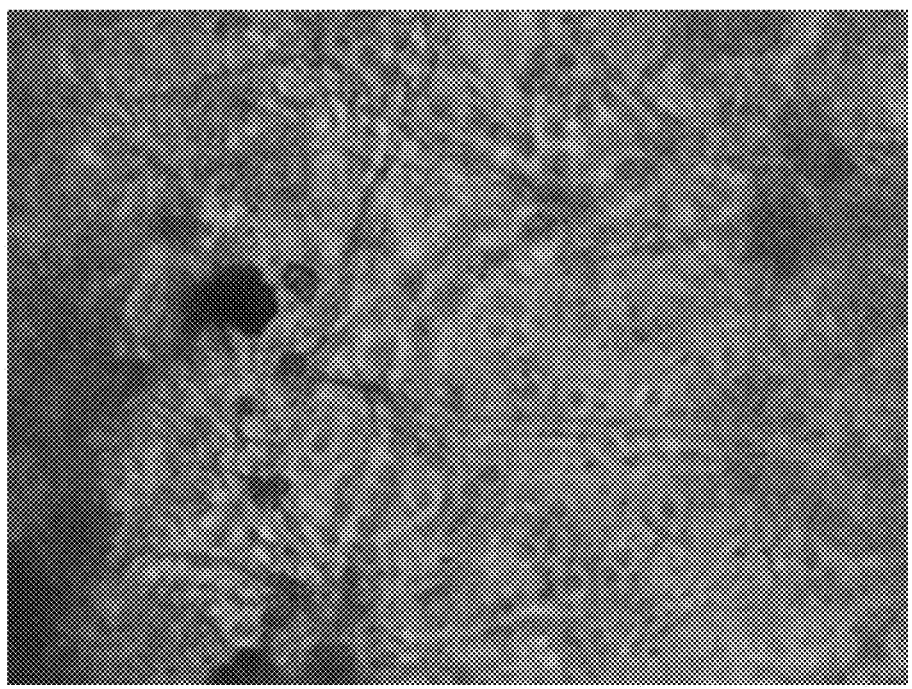

Paprika powder (without preservatives) was used for colouring the mycelium biomass. 100 g/L concentrated suspension was prepared and autoclaved for 15 min at 121° C. In four different flasks, paprika suspension was added in two concentrations 5 g/L and 10 g/L at two different time frames: beginning of fermentation (day 0) and day 5 of fermentation. The same procedure for fermentation and harvesting was conducted as mentioned in the previous examples. For the flasks where the suspended paprika was added at day 0, the colour disappeared within 24-48 hours and the mycelium biomass turned out to be neutral in colour. Regarding the flasks where the colour was added at day 5, the mycelium biomass turned out to have a light or dark orange shade depending on the concentration used i.e., 5 g/L and 10 g/L, respectively. Experimental results are shown in FIG. 4.

Figure 5A:
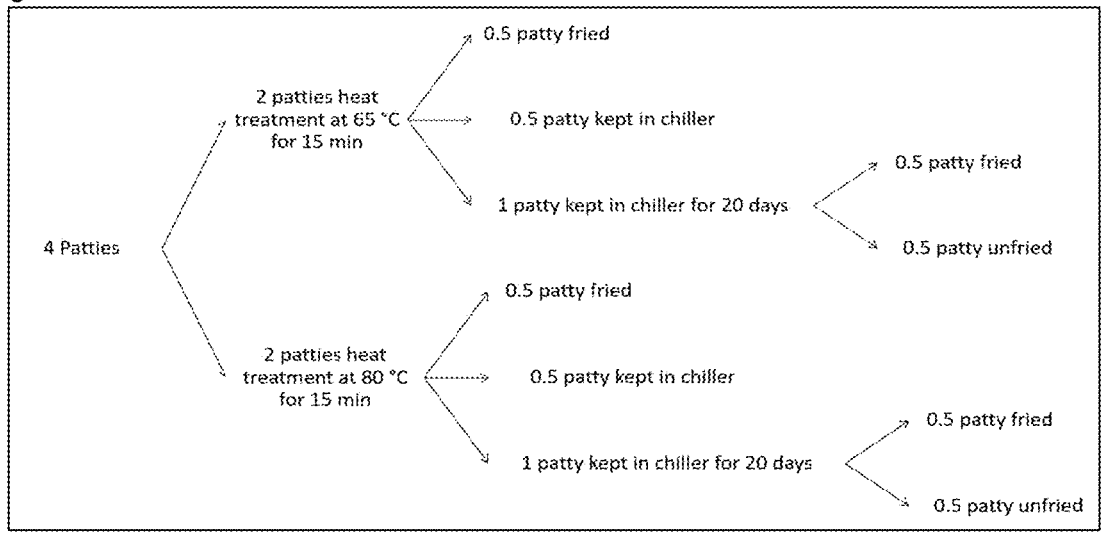
FIGS. 5A-5C FIG. 5A) The biomass was made into 4 patties of 50 g each and processed according to the shown conditions (0.5 patty fried directly after cooking at two different conditions, 0.5 patty kept in the chiller, and 1 patty kept in the chiller for 20 days, from which 0.5 patty was fried and the other was not.) FIGS. 5B-5C) comparison of fried and unfried patties made from the biomass coloured after fermentation (FIG. 5B) and during fermentation (FIG. 5C, more intense colour). Average RGB.

Example 4. Comparison of Browning Performance of Biomass Coloured During Fermentation and After Fermentation Using Astaxanthin as a Colourant The colouring experiment was designed to compare the colouring performance by allowing the same contact time of biomass with colourant astaxanthin as discussed in Example 1. The biomass was formed into 4 patties of 50 g each and processed according to scheme shown in FIG. 5A for both scenarios (colouring during or after fermentation). The patties which were kept in the chiller were kept at 4° C. All other samples were kept in vacuum conditions in bags.

Figure 5B:
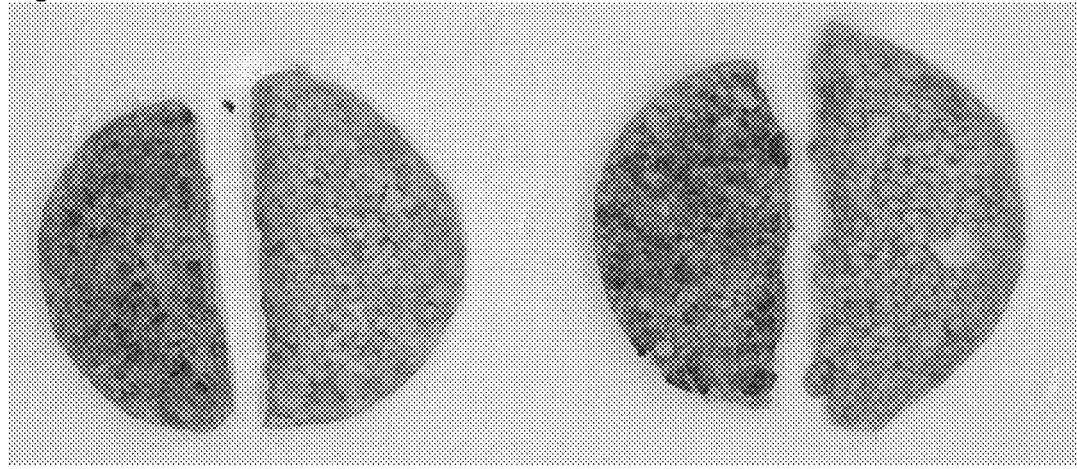
Figure 5C:
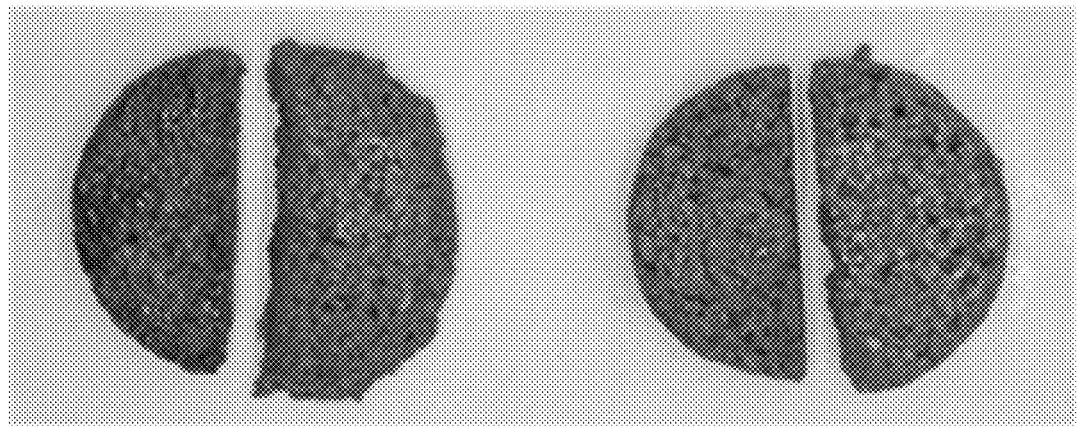

The cooking performance of the difference biomasses was tested. FIG. 5BC shows the comparison of fried and unfried patties made from the biomass coloured after fermentation (B) and during fermentation (C, more intense colour). The patties were cooked at 65° C. for 15 minutes (A, left) and 80° C. for 15 minutes (A, right) (heat treatment) before frying. The bottom picture shows the patties of the same treatment, but for biomass coloured during fermentation. The colouring performance and browning effect of patties made from biomass coloured during fermentation was significantly superior compared to patties made from biomass coloured after fermentation. In other words, the browning effect is more homogenous with an appealing colour for consumption.

Figure 6A:
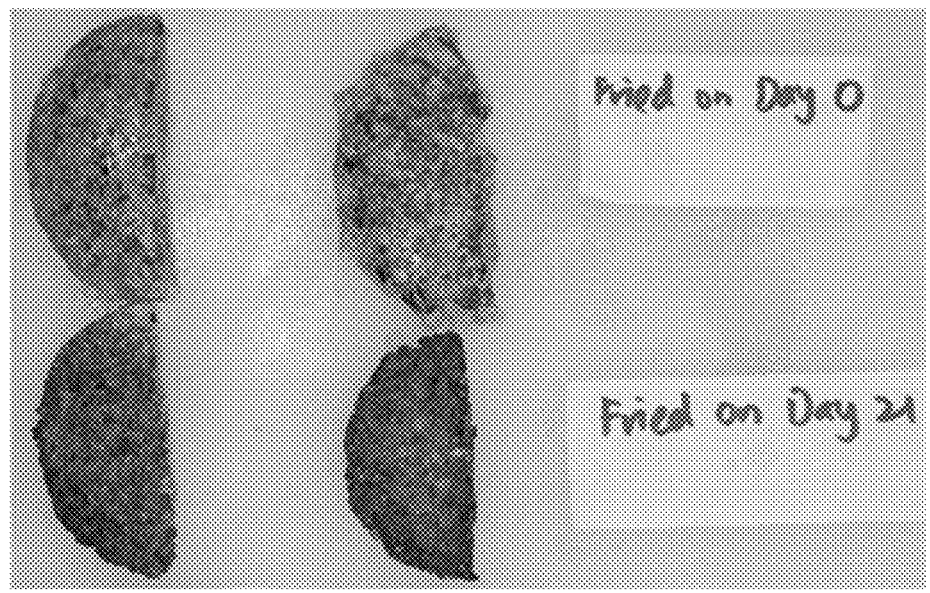
FIGS. 6A-6B Comparison of fried patties at day 0 or day 21 at different cooking conditions ($1^{st}$ column: 65° C. for 15 min; $2^{nd}$ column 80° C. for 15 min). The colouring performance and browning effect of patties made from biomass coloured during fermentation (FIG. 6B) was significantly superior compared to patties made from biomass coloured after fermentation (FIG. 6A) at day 0. Both showed improved browning effect. Average RGB: top left to right: (167, 99, 49); (155, 86, 59), 2nd row from left to right: (145, 72, 40); (143, 55, 27), 3rd row from left to right: (112, 58, 46); (135, 50, 27), bottom from left to right: (110, 54, 48); (105, 57, 53).
Figure 6B:
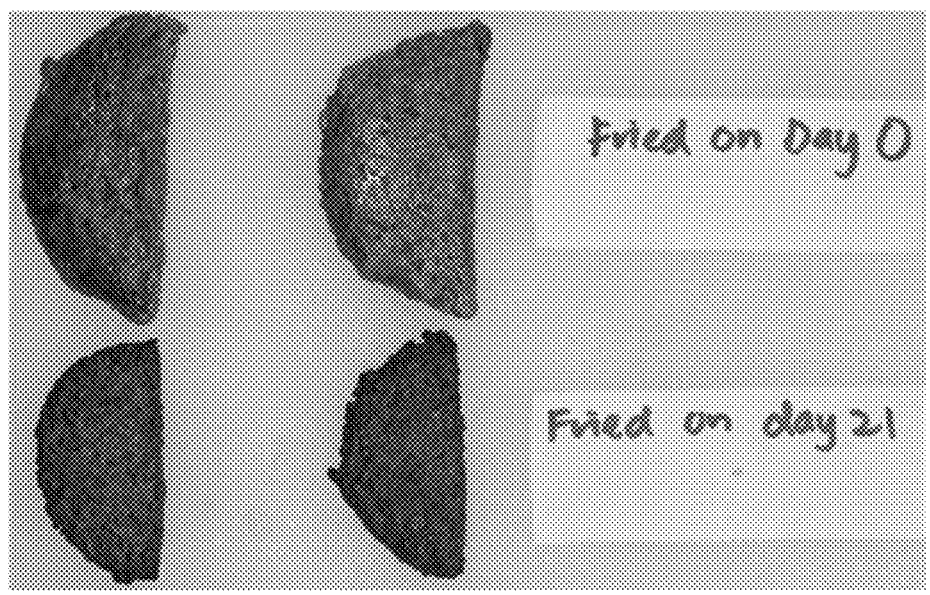
Figure 7:
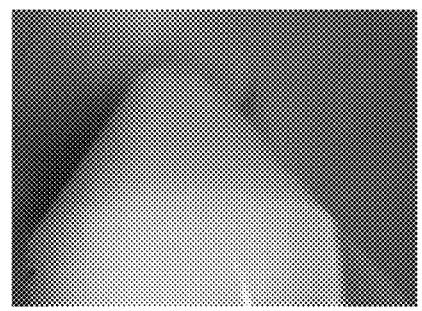
FIG. 7. Biomass with its natural whitish colour. Average RGB (228, 226, 226).

All samples were stored for 21 days at 4° C. and the unfried patties were fried under the same condition. The resulting colouring performance and browning effect is shown in FIG. 6. The top figure shows the half patties made from biomass coloured after fermentation which were fried on Day 0 and Day 21 (after the storage period) for 5 minutes at lowest level of the heating stove (level 1). The bottom figure shows the half patties made from biomass coloured during fermentation stored and fried in the same method.

The difference in colour performance and browning effect between the samples of no resting period and samples with 21 days of resting was significant. The browning performance was significantly improved in both scenarios (during and after fermentation) after a storage period of 21 days. Water was lost during the storage period and a better crusting effect was observed in both half patties made from both scenarios. The colour was not altered during the storage period showing that the colour is stable throughout this period.

Example 6. Bioreactor Setup

Figure 8:
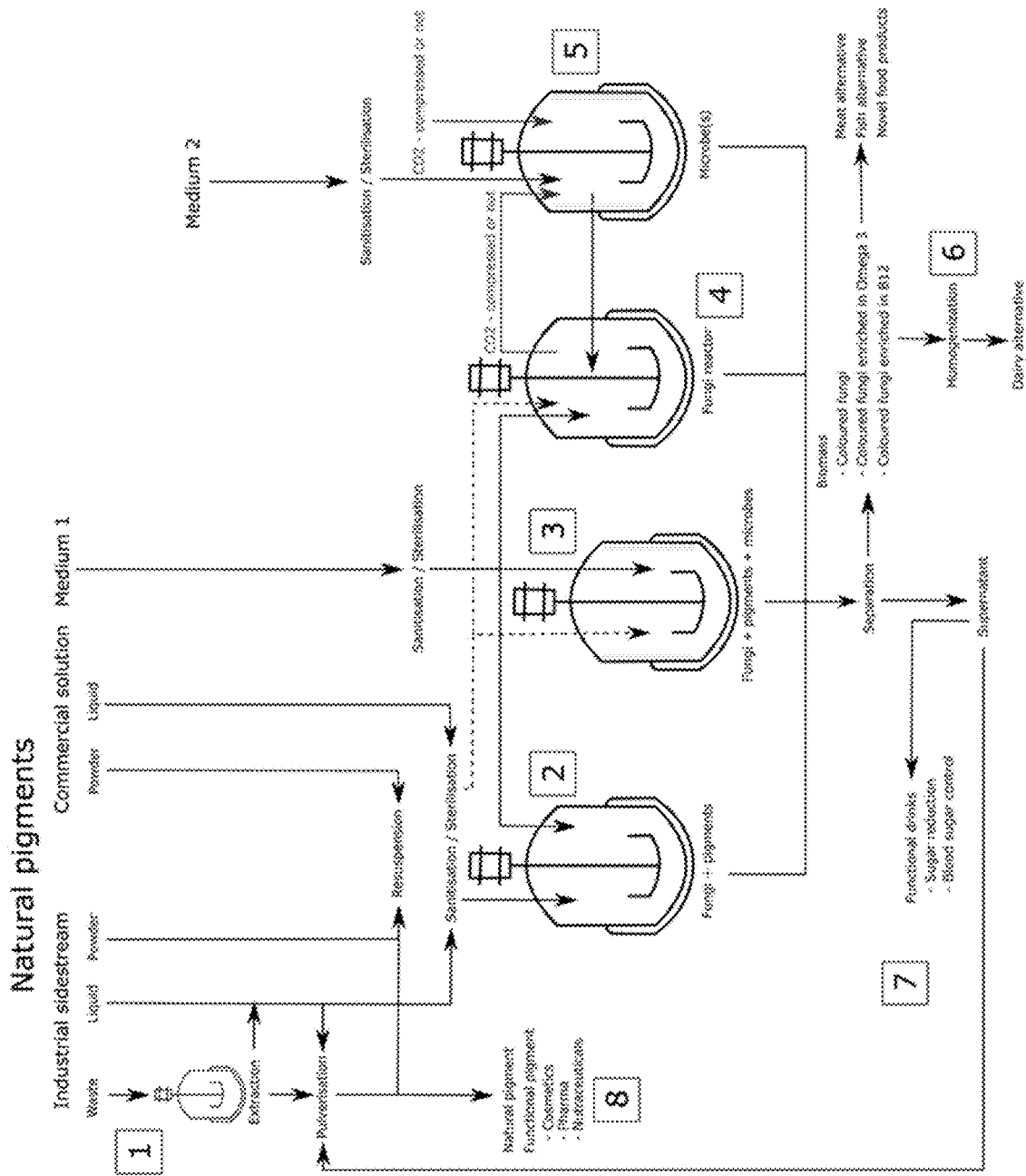
FIG. 8. Exemplary experimental setup for the method of the present invention.

FIG. 8 presents an exemplary bioreactor setup for executing the method of the present invention.

[1] Preparation of Pigment Solution

In the first step, pigment solution is prepared. This step aims at providing the natural pigment(s) that will be used in the fermentation afterwards. The simplest way to achieve this goal would be to buy commercial powders or liquid products containing natural pigments such as carotenoids, chlorophyll, phycobilins, anthocynins or any others. Alternatively, other materials can be pulverized before addition to the medium if necessary. Ideally, those compounds bring the colour to the mycelium but can also be advantageous in terms of nutrition or shelf-life stability of product (e.g., antioxidants, omega-3 fatty acids). The powder can also be lyophilized or liquid suspension of microbes such as algae.

Another way to prepare the pigments for fermentation would be to use industrial sidestreams that contains those pigments. If the sidestream used is already a liquid that contains the pigment and can be directly added to the fermentation medium. Its colour can probably be fine-tuned by changing the temperature and time of sterilization or can remain the original one if the sidestream is sterilized using sanitizing agents (e.g., HClO). The second possibility is that the sidestream is a powder and it can be resuspended in liquid and used as the liquid sidestream afterwards. Finally, we can also get other solid sidestreams such as vegetable wastes from farms or others and we will have to extract the pigments using a solvent and pulverized it afterwards.

[2] Fungal Fermentation on Coloured Culture Medium

Mixing of different pigments is also an option to get fine-tuned colours. Same sidestreams can also have different colour shades. For instance, cocoa powders have different browning grades and that is probably related to different browning processing in the production of cocoa. The pigment would preferably come from fruits, vegetables and plants but it can also be "mineral pigments" that contains trace elements interesting for fermentation.

After preparing a pigment solution, the solution is either sterilized or sanitized and added to the fermentation medium. It can also be added to the medium before sterilization or sanitization, depending on what is the most efficient way to reach the desired colour. The fungi is then grown on the coloured medium and either assimilate the pigment or grow on it during fermentation—depending of the pigment nature.

[3]-[5] Co-fermentation of Edible Fungi and Coloured Microbes

Another option to colour the fungal biomass is to bring the colour by co-fermenting at least one fungal strain with at least one other microbe that is producing a pigment either (i.e., a coloured microbe) intracellularly or extracellularly. In that case, the at least one pigment producing microbe is added to the fermenter at a time point that enables efficient colouring of the fungal biomass but does not lead to overgrowth of the said microbes in the fermenter, meaning that the at least one microbe added does not deplete the medium nutrients before the at least one fungal strain has had enough time to grow to a desired extent. The added pigment producing microbes can be fungi, bacteria, archaea, algae, or any microbes able to produce pigments. In a specific embodiment, even colours from an animal origin can be used to colour the fungal biomass. Preferably, the at least one pigment producing microbe added to the fermenter is not a GMO-organism, but GMO-organisms are not excluded. Alternatively, the medium used to do the co-culture also contains at least one other pigment that can be added as a powder or a solution as described in step [2] and enables the fine-tuning of the final colour of the fungal mycelium. Depending on the time required to have a significant amount of biomass of the at least one pigment producing microbes, it is also possible to start fermentation with the at least one pigment producing microbe and add the at least one fungal strain of interest later to the fermenter.

If the growth conditions (medium, pH, optimal temperature, shear sensitivity, etc.) required by the at least one pigment producing microbe are too different from those of the at least one chosen fungal strain or if the growth time from the at least one pigment producing microbes differs too much from the growth time of the at least one fungal strain, fermentation can be done in two separate fermenters and the at least one pigment producing microbe is added at a given time to the fermenter containing the at least one fungal strain [4] [5]. This configuration can for instance be advantageous to use the $CO_2$ produced during fungal fermentation in its normal state or after compression to grow $CO_2$ fixing microbes like algae or cyanobacteria more efficiently in a separate fermenter before adding them to the fermenter with the at least one fungal strain [5]. Similarly, $CO_2$ captured from other sources can be added to the second fermenter to boost growth of $CO_2$-fixing microbes even further, thus resulting in a carbon neutral or carbon negative process. It is also envisaged to use commercial $CO_2$ as input for the growth of the at least one pigment producing microbes [5]. If required, the fermenter can also be equipped with different light system able to work at different wavelengths to stimulate the growth of certain type of microbes (e.g., algae) or the production of specific compounds (e.g., vitamin D).

[6] Separation and Processing of Biomass

After the fermentation, the biomass is separated by filtration, centrifugation, or other state-of-the-art techniques, washed with water and concentrated to a concentration suitable for the production of a food product. The biomass can be pure mycelium that incorporate soluble pigments or mycelium grown on solid (pigment) particles or a mixture of mycelium and other colourful microbes. Depending on the composition, it can be enriched in vitamins, especially B12, antioxidants and in omega-3 fatty acids or other fatty acids as well.

[7] Recovery and Use of the Supernatant as Beverages, e.g., Alcoholic Drinks or Sweet Healthy Drinks After separation of the fermentation broth, the supernatant has a residual colour and an appealing taste and aroma (e.g., almondy, maple, raspberry, kiwi, etc.) because of the volatile compounds that mushroom mycelium is able to produce during fermentation. This supernatant can serve as basis for soft drinks or alcoholic drink. The latter can also be supported by the choosing fermentation conditions and production strains in a way that alcohol production is enhanced during the process and increase in the fermentation broth over time, just as can be observed in typical beer fermentation with brewing yeast. This liquid solution is then further processed to adjust the taste either by adding additional ingredients (e.g., sugar, alcohol, acidifying agent, etc.), modifying compounds enzymatically or adjusting the level of alcohol by methods known by the skilled person (e.g., distillation). Mushrooms mycelia are also known for their ability to produce antioxidants, exopolysaccharides, functional peptides, and other metabolites that can be relevant to tackle health aspects such as regulation of blood sugar levels. Hence, the produced drinks can also find application as health drinks in the future.

[8] Drying of the Supernatant for Other Applications

Alternatively, the functional compounds found in the supernatant obtained after fermentation can also be purified by methods known to the skilled person (e.g., preparative chromatography, crystallization, solvent extraction, etc.) and dried to deliver high-purity solutions for the nutraceutical and pharmaceutical industry. Another interesting aspect could also be the drying of the coloured supernatant to integrate it as a powder in functional cosmetical composition, in particular for skin care applications. In fact, exopolysaccharides, antioxidants, functional peptides, and other fungal based metabolites have known a rising interest in the cosmetic industry in the past years and delivering a coloured material with functional properties will be of interest for this industry. Similarly, functional compounds found in the coloured extracts produced from the sidestreams in step [1] could also be recovered in the same way and found applications in the nutraceutical, pharmaceutical and pharmaceutical industries.

TABLE 1

Example of 0.9 g/L Astaxanthin based on a triplicate in the washing water at different time points compared to the supernatant at the end of fermentation - calculated from the absorbance at 530 nm

| | Astaxanthin (mg/L) | | | |
|---|---|---|---|---|
| Sample | Supernatant | Washing water (2 hrs) | Washing water (4 hrs) | Washing water (6 hrs) |
| Astaxanthin-0.9 g/L | — | 0.6 | 0.5 | 0.1 |

[3] Content Analysis

TABLE 2

Astaxanthin content in the supernatant and in the mycelium biomass at the end of fermentation

| Sample | Wet biomass [g] | Astaxanthin added [mg] | Astaxanthin detected in biomass [mg/100 g wet biomass] | Astaxanthin detected in supernatant [mg/100 g supernatant] | Astaxanthin accumulated [mg] | Astaxanthin accumulated [%] |
|---|---|---|---|---|---|---|
| Astaxanthin −0.9 g/L | 17.9 | 4.5 | 18.83 | <0.05 | 3.36 | 74.7 |
| Astaxanthin −1.8 g/L | 18.7 | 9 | 34.62 | <0.05 | 6.49 | 72.1 |

Example 6. Leaching Test

The stability of the colour is investigated with a UV-vis absorption technique using photolab 7600 UV-Vis. The coloured biomass with astaxanthin is soaked in water. Samples are taken every 1 hour up to 12 hours and another sample is taken after 24 hours and placed in the spectrophotometer to generate a UV-vis spectrum. The UV-vis spectrum of the control solution (water without soaked biomass) shows a high compatibility with the spectra of the solution collected up to at least 24 hours indicating that the colour is not leaching in the solution.

Example 7. Astaxanthin as a Colourant: Stability, Content Analysis, Time of Addition, and Scale-up

[1] Addition of Astaxanthin with Different Concentrations at Deceleration Phase

As an example, 0.9 g/L and 1.8 g/L of Astaxanthin powder (5 wt. % astaxanthin) was added in the deceleration phase of fermentation. The fermentation was conducted aerobically in a 100 ml shake flask. The difference in colour shows that the colour intensity of red can be accordingly controlled based on the added concentration (FIG. 9).

[2] Washing Protocol

Figure 9:
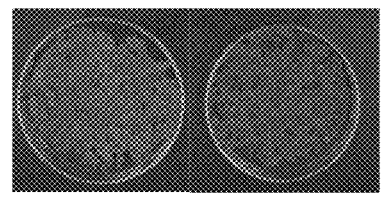
FIG. 9. Mycelium biomass with 0.9 g/L astaxanthin (left, colour: light orange, slightly red) vs 1.8 g/L astaxanthin (right, colour: red) added in the deceleration phase.
Figure 10:
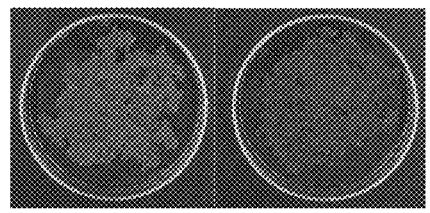
FIG. 10. Mycelium biomass with 0.9 g/L astaxanthin (left, colour: light orange, slightly red) vs 1.8 g/L astaxanthin (right, colour: red) after 24 hrs of soaking in tap water.
Figure 11:
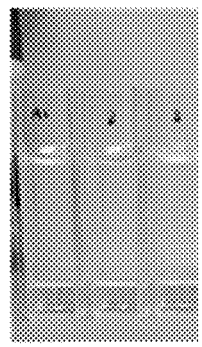
FIG. 11. Example of washing water after 2 hrs, 4 hrs, and 6 hrs for samples with 0.9 g/L Astaxanthin.

The harvested biomass as shown in FIG. 9 was washed with tap water to mimic the downstream process of large-scale activities and to check for the stability of the colour in case of storage in solution. Therefore, the biomass was soaked in tap water and the spectrophotometer measurements were recorded for the washing water after 2 hrs, 4 hrs, 6 hrs. Table 1 below shows the amount of astaxanthin leached into the solution, which was also shown to be negligible in FIG. 11 to the naked eye. The same observations were observed after 24 hrs (see FIG. 10).

Table 2 shows that for both concentrations of Astaxanthin (0.9 g/L and 1.8 g/L) added in the deceleration phase, the amount of astaxanthin accumulated in the biomass is comparable with an average of 73.4%. This eventually helps in estimating and quantifying the amount of colourant needed to reach desired product properties and composition.

[4] Different Addition Times

Figure 12:
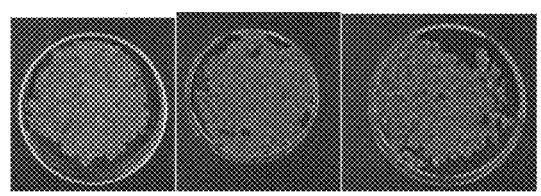
FIG. 12. Mycelium biomass with Astaxanthin added at lag phase (X1), exponential phase (X3), and deceleration phase (X2) (from left to right, colours from left to right: white dotted with brown/red; light orange/pink; red).

FIG. 12 shows mycelium biomass resulting from the addition of Astaxanthin at added at lag phase (X1), exponential phase (X3), and deceleration phase (X2). We can observe that the later we add the colourant, the more retained the colour is. This confirms that adding astaxanthin at the deceleration phase is preferable over the log phase or exponential phase. Additionally, this is cost efficient as the later we add the colourant, less pigment is needed to reach a targeted product composition.

[5] Heating Test

TABLE 3

Astaxanthin concentration in the water at different time points at 85° C. - calculated from the absorbance at 530 nm

| Time [min] | Abs | Astaxanthin [mg/L] |
|---|---|---|
| 10 | 0.013 | — |
| 40 | 0.037 | — |
| 60 | 0.048 | — |
| 80 | 0.092 | 0.34 |

Figure 13:
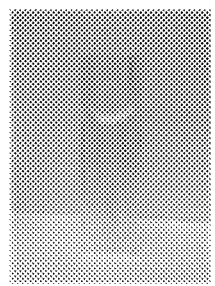
FIG. 13. Water sample after heating the biomass for 80 mins.

The aim of this trial was to mimic the impact of cooking on the colour of the biomass. The biomass was soaked in tap water and heated to 85° C. As it can be observed from the table above, no colour loss is detectable until 60 mins showing that the colour does not leach during cooking. This is also shown in FIG. 13, showing that colouration of water after 80 minus heating as described hereinabove is barely visible.

[6] Colouring After Fermentation i.e., After Harvesting of Biomass

To mimic the addition of Astaxanthin at the deceleration phase, 100 ml flask (50 ml medium) was inoculated. At X2, the biomass was harvested and soaked in 50 ml of 0.9 g/L Astaxanthin. One was placed in the fridge at 4° C. and the other at 25° C. in the incubator for 2.5 days to have the same total incubation time of 6.5 days.

The coloured biomass was then retrieved and washed 3 times, after 2 hrs, 4 hrs, and 24 hrs to understand the stability of the pigment as compared to colouring at deceleration phase of fermentation.

TABLE 4

Example of Astaxanthin concentration in water at different time points from soaking at 4° C. - calculated from the absorbance at 530 nm

| Sample | Astaxanthin (mg/L) | | |
| --- | --- | --- | --- |
| | Washing water (2 hrs) | Washing water (4 hrs) | Washing water (24 hrs) |
| Astaxanthin-fridge | 2.82 | 1.48 | 1.55 |

Figure 14:
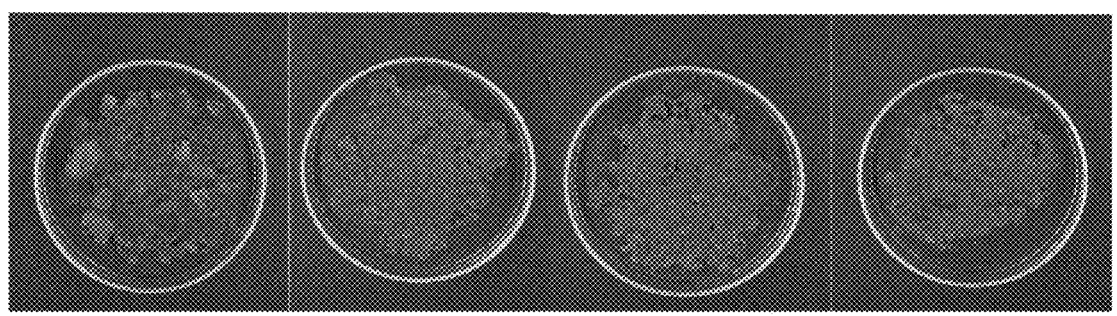
FIG. 14. Biomass samples coloured with 0.9 g/L Astaxanthin after fermentation at 25° C.—biomass before washing and after 2 hrs, 3 hrs, and 6 hrs respectively from left to right.
Figure 15:
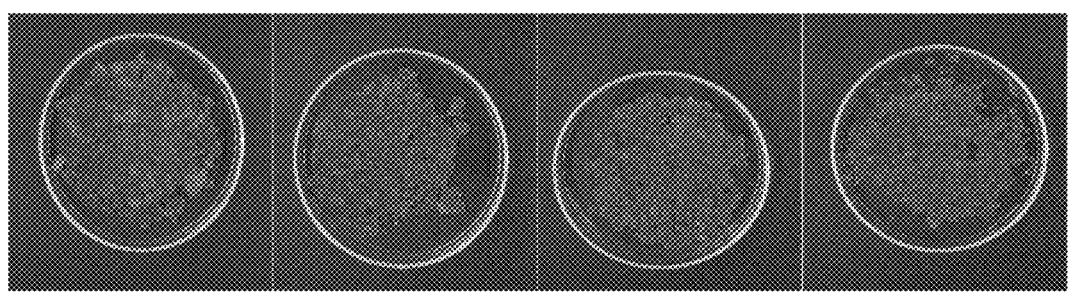
FIG. 15. Biomass samples coloured with 0.9 g/L Astaxanthin after fermentation at 4° C.—biomass before washing and after 2 hrs, 4 hrs, and 6 hrs respectively from left to right.

According to the figures, samples cannot be macroscopically differentiated between the biomass soaked at 4° C. from the one soaked at 25° C. However, according to the table above, it is clear that the colour is less stable using this method of colouring (i.e., after fermentation). In addition, it was obvious in the laboratory that the biomass coloured after fermentation did not retain the colour well, as astaxanthin was leaching on the gloves while working with said coloured biomass, whether soaked at 4° C. or 25° C. Additionally, it is clear in the first picture of the FIGS. 14 and 15, that the biomass was not coloured homogeneously, as white chunks of biomass are still remained to be seen.

[7] Scaling Up Fungal Growth with Astaxanthin

Figure 16:
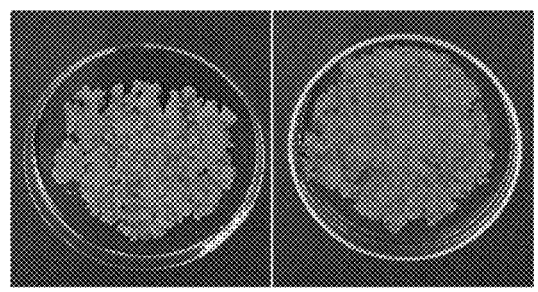
FIG. 16. Mycelium biomass supplemented with 0.9 g/L Astaxanthin at time 0 from a 1 L fermenter (left, colour: whitish/light brown) vs 100 ml flask (right, colour: white dotted with brown/red).
Figure 17:
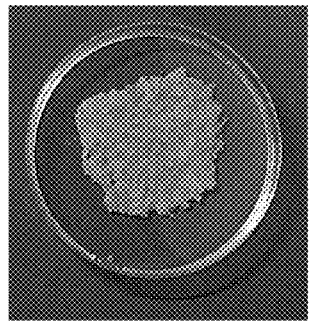
FIG. 17. Mycelium biomass supplemented with 0.9 g/L Astaxanthin during deceleration phase (X2) in a 1 L fermenter harvested.
Figure 18:
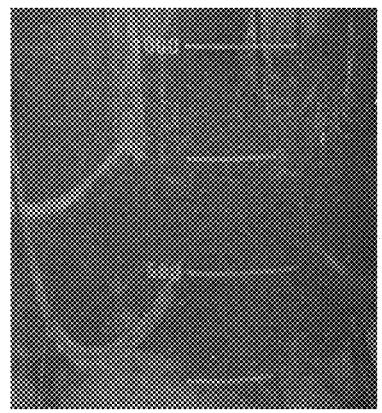
FIG. 18. Inner view of a 1 L fermenter supplemented with 0.9 g/L Astaxanthin during deceleration phase (X2).

The mycelium being fermented in a 1 L fermenter with the addition of Astaxanthin at time 0, with a controlled dissolved oxygen (DO), agitation and aeration also showed degradation of astaxanthin compared to when it is added at the deceleration phase. FIGS. 16 and 17 show that the process is scalable, where in the first figure it is clear that the pigment degrades over time similarly as confirmed on a flask scale, however with a slightly higher intensity. Taking into consideration the fact that in a fermenter, additional parameters are controlled compared to the flask, such as, pH, and dissolved oxygen (which can have a significant impact on the behavior of the cells). The result is relatively comparable, still proving that adding the pigment during the deceleration phase yields a more homogeneously coloured biomass and less Astaxanthin decomposition as seen in FIGS. 17 and 18.

Example 8. Lycopene

Figure 19:
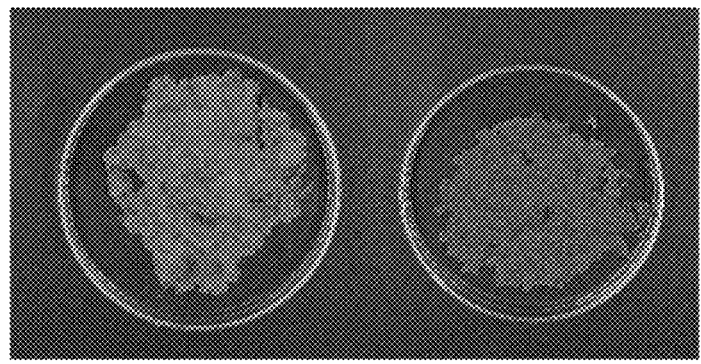
FIG. 19. Mycelium biomass with 1 g/L lycopene added at day 0 (left, colour: white dotted with brown/red) vs in the deceleration phase (right, colour: orange/red).

As shown in FIG. 19, lycopene powder (10 wt. % lycopene) was added either at day 0 or during deceleration phase. Addition of lycopene during the deceleration phase yields a more coloured biomass, same as in the case of astaxanthin, where the later the colourant is added (i.e., towards the decelaration phase), the more intense the retention of the colour is (i.e., higher colour intensity, lower leaching).

Example 9. Co-Fermentation of Fungi

Figure 20:
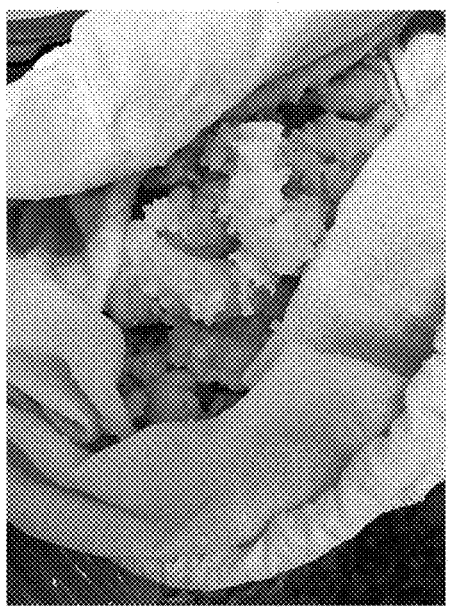
FIG. 20. Mycelium biomass from cofermentation with a species of *Rhodotorula* genus.

*Pleurotus pulmonarius* and species comprising of at least *Rhodotorula* genus were fermented aerobically together. The *Rhodotorula* is a genus of pigmented yeasts, part of the division Basidiomycota. The *Rhodotorula* was added from the beginning as it has a slower growth rate than *Pleurotus pulmonarius*. In FIG. 20 above we can observe a salmon-like coloured mycelium biomass, which is suitable for fish analogues. The same co-fermentation concept can be implemented with algae strains such as *Haematoccus pluvialis*, *Chlorella vulgaris* and/or with cyanobacteria.

Example 10. Microalgae as a Colourant and its $CO_2$ Fixation

*Pleurotus pulmonarius* was cultivated aerobically in a 1 L fermenter. The fermentation was supplied with air of 0.05% $CO_2$ composition. The exhaust of the fermenter has been split into two, one supplied to another fermenter where microalgae is being cultivated and one connected to a gas analyzer to quantify the $CO_2$ in the exhaust air of the fermenter. The second fermenter with microalgae species *Haematococcus pluvialis* (non-ruptured) is cultivated in BG11 commercial medium supplemented with a trace element mixture and is supplied with the exhaust of the *Pleurotus pulmonarius* fermentation (as mentioned above). It is also equipped with an LED light (3000 K warm). The exhaust of this second fermenter is connected to a gas analyzer to quantify the $CO_2$ in the exhaust air and calculate accordingly the $CO_2$ fixed by the microalgae. FIG. 21 shows the trend of the $CO_2$ percentage (by volume) fixed by the microalgae, which is calculated by subtracting the percentage of the $CO_2$ in the exhaust of the microalgae culture from the percentage of the $CO_2$ input, which is fed from the exhaust of the *Pleurotus pulmonarius* mycelium fermentation. The trend of the $CO_2$ fixed is shown in this figure to be increasing for a time window shown during the microalgae culture.

Scenario 1: After pigmentation of *Haematococcus pluvialis*, the microalgae broth containing microalgae is added at the deceleration phase of an additional fermenter of *Pleurotus pulmonarius* running in parallel. The obtained biomass is green and enriched with omega 3 fatty acids.

Scenario 2: After the *Haematococcus pluvialis* starts pigmenting, stress is induced by nitrogen deprivation or salts addition to produce in situ astaxanthin which is then added to the deceleration phase of the *Pleurotus pulmonarius* fermentation leading to a reddish biomass.

Example 11. Kombucha Beverage Preparation 850 g of supernatant was mixed with 150 g mycelium (wet mass) and was heated at 95° C. for 60 mins under rigorous stirring at 650 rpm. The mycelium is then filtered out up to 99% after cooling down the mixture followed by adding 17 wt. % of raw cane sugar. Next, 100 g of unpasteurized kombucha SCOBY liquid (Symbiotic Culture of Bacteria and Yeast) was added. All liquids were combined into a jar or fermentation vessel, with 1 piece of kombucha SCOBY (125 g) into the liquid, and the jar was covered with a cloth and kept at 22° C. After 7 days, the SCOBY was removed and the liquid was strained, diluted with black tea to reach a sugar content of 8° Bx and then bottled.

Further examples and/or embodiments of the present invention are disclosed in the following numbered items.

1. A method for the production of a composition comprising a fungal biomass, characterized in that said composition has a particular colour, the method comprising the steps of:
   (a) providing a growth medium;
   (b) providing at least one fungal strain;
   (c) cultivating the at least one fungal strain in the growth medium;
   (d) supplementing the growth medium with at least one additive that gives rise to the colour of the composition;
   (e) further cultivating the at least one fungal strain in the growth medium supplemented with the at least one additive that gives rise to the colour of the composition; and
   (f) harvesting from the growth medium the composition comprising the fungal biomass characterized in that said composition has a particular colour;
   wherein the particular colour is due to the at least one additive supplemented in step (d).
2. The method of item 1, wherein the at least one fungal strain is an edible fungal strain.
3. The method of item 1 or 2, wherein the at least one fungal strain is selected from Basidiomycota and Ascomycota.
4. The method of any one of items 1 to 3, wherein the at least one fungal strain is selected from Pezizomycotina and Agaromycotina.
5. The method of any one of items 1 to 4, wherein the at least one fungal strain is selected from Peziomycetes, Agaricomycetes, and Sordariomycetes.
6. The method of any one of items 1 to 5, wherein the at least one fungal strain is selected from Pezizales, Boletales, Cantharellales, Agaricales, Polyporales, Russulales, Auriculariales, Sordoriales, and Hypocreales.
7. The method of any one of items 1 to 6, wherein the at least one fungal strain is selected from Morchellaceae, Tuberaceae, Pleurotaceae, Agaricaceae, Marasmiaceae, Cantharellaceae, Hydnaceae, Boletaceae, Meripilaceae, Polyporaceae, Strophariaceae, Lyophyllaceae, Tricholomataceae, Omphalotaceae, Physalacriaceae, Schizophyllaceae, Sclerodermataceae, Ganodermataceae, Sparassidaceae, Hericiaceae, Bondarzewiaceae, Cordycipitaceae, Auriculariaceae, Sordoriaceae, Nectriaceae and Fistulinaceae.
8. The method of any one of items 1 to 7, wherein the at least one fungal strain is *P. pulmonarius P. ostreatus, P. citrinopileatus* or *P. salmoneostramineus* or wherein the at least one fungal strain is *M. esculenta, M angusticeps, M. deliciosa,* or *M. rufobrunnea*.
9. The method of any one of items 1 to 8, wherein the at least one fungal strain is *P. pulmonarius*.
10. The method of any one of items 1 to 9, wherein the growth medium further comprises vitamin B12 and/or omega-3 fatty acid(s).
11. The method of any one of items 1 to 10, wherein the at least one additive that gives rise to the colour of the composition comprises a powder, wherein preferably said powder forms dispersed phase when being supplemented to the growth medium in step (d).
12. The method of item 11, wherein the powder is a cocoa powder, a duckweed powder, a spirulina powder, a paprika powder, a turmeric powder, a heme powder or a beet powder, or a combination thereof.
13. The method of item 11 or 12, wherein the composition comprising the fungal biomass comprises mycelium bound to the particles of the powder dispersed in the growth medium, wherein preferably the growing mycelium traps the particles of the powder dispersed in the growth medium.
14. The method of item 13, wherein the particles of the powder bound to the mycelium cannot be separated from the mycelium, preferably by washing, without disrupting the mycelium structure, preferably without disrupting the fungal cells.
15. The method of item 13 or 14, wherein the particles of the powder bound to the mycelium constitute up to 25% w/w of the composition comprising the fungal biomass.
16. The method of any one of items 11 to 15, wherein step (d) is performed before the commencement of step (c).
17. The method of any one of items 1 to 10, wherein the at least one additive that gives rise to the colour of the composition comprises a colourant that is assimilated by the at least one fungal strain.
18. The method of item 17, wherein the assimilation of the colourant by the at least one fungal strain is dependent on the oxygen availability to the at least one fungal strain.
19. The method of item 17 or 18, wherein step (e) is performed for not more than 72 hours, preferably not more than 48 hours.
20. The method of any one of items 17 to 19, wherein the colourant is a terpene compound.
21. The method of item 20, wherein the colourant is astaxanthin or a derivative thereof.
22. The method of any one of items 1 to 10, wherein the at least one additive that gives rise to the colour of the composition comprises a coloured microorganism.
23. The method of item 22, wherein the coloured microorganism is a microorganism selected from red algae, green algae, brown algae and cyanobacteria.
24. The method of item 22 or 23, wherein the composition comprising a fungal biomass further comprises a biomass of a coloured microorganism, preferably selected from red algae, green algae, brown algae and cyanobacteria.
25. The method of any one of items 1 to 24, wherein the supplementing in step (d) is done in the lag phase, in the acceleration phase, in the exponential phase, in the deceleration phase, or in the stationary phase of the biomass growth, preferably wherein the supplementing in step (d) is done in the deceleration phase or in the exponential phase of the biomass growth, more preferably wherein the supplementing in step (d) is done in the deceleration phase of the biomass growth.
26. The method of any one of items 1 to 25, wherein the supplementing in step (d) is done in the exponential phase, preferably wherein the cultivation is performed as submerged fermentation performed as a continuous process.
27. The method of any one of items 1 to 65, further comprising the step of recovering a supernatant in step (f).
28. A composition obtainable according to the method of any one of items 1 to 27.
29. A food product comprising the composition of claim 28.
30. The food product of item 29, further comprising an additive selected from preservatives, antioxidants and acidity regulators, thickeners, stabilisers and emulsifiers, pH regulators and anti-caking agents, flavor enhancers, improving agents, stabilizers, thickening agents, colours, and/or glazing agents and sweeteners.
31. Use of the composition of item 28 in the production of a food product.
32. A supernatant obtainable according to item 27.
33. Use of the supernatant of item 32 in the production of a food product.

Further examples and embodiments of the present invention are disclosed in the following numbered paragraphs:
1. A method for the production of a composition comprising a fungal biomass, characterized in that said composition has a particular colour, the method comprising the steps of:
   (a) providing a growth medium;
   (b) providing at least one fungal strain;
   (c) cultivating the at least one fungal strain in the growth medium;
   (d) supplementing the growth medium with at least one additive that gives rise to the colour of the composition;
   (e) further cultivating the at least one fungal strain in the growth medium supplemented with the at least one additive that gives rise to the colour of the composition; and
   (f) harvesting from the growth medium the composition comprising the fungal biomass characterized in that said composition has a particular colour;
   wherein the particular colour is due to the at least one additive supplemented in step (d).
2. The method of paragraph 1, wherein the at least one fungal strain is an edible fungal strain, preferably wherein the at least one fungal strain is selected from Basidiomycota and Ascomycota, more preferably wherein the at least one fungal strain is selected from Pezizomycotina and Agaromycotina,
   even more preferably wherein the at least one fungal strain is selected from Peziomycetes, Agaricomycetes, and Sordariomycetes,
   even more preferably wherein the at least one fungal strain is selected from Pezizales, Boletales, Canthar- ellales, Agaricales, Polyporales, Russulales, Auriculariales, Sordoriales, and Hypocreales, even more preferably wherein the at least one fungal strain is selected from Morchellaceae, Tuberaceae, Pleurotaceae, Agaricaceae, Marasmiaceae, Cantharellaceae, Hydnaceae, Boletaceae, Meripilaceae, Polyporaceae, Strophariaceae, Lyophyllaceae, Tricholomataceae, Omphalotaceae, Physalacriaceae, Schizophyllaceae, Sclerodermataceae, Ganodermataceae, Sparassidaceae, Hericiaceae, Bondarzewiaceae, Cordycipitaceae, Auriculariaceae, Sordoriaceae, Nectriaceae and Fistulinaceae,
   even more preferably wherein the at least one fungal strain is *P. pulmonarius P. ostreatus, P. citrinopileatus* or *P. salmoneostramineus* or wherein the at least one fungal strain is *M. esculenta, M angusticeps, M. deliciosa*, or *M. rufobrunnea*,
   even more preferably wherein the at least one fungal strain is *P. pulmonarius*.
3. The method of paragraph) or 2, wherein the growth medium further comprises vitamin B12 and/or omega-3 fatty acid(s).
4. The method of any one of paragraphs 1 to 3, wherein the at least one additive that gives rise to the colour of the composition comprises a powder, wherein preferably said powder forms dispersed phase when being supplemented to the growth medium in step (d).
5. The method of paragraph 4, wherein the powder is a cocoa powder, a duckweed powder, a spirulina powder, a paprika powder, a turmeric powder, a heme powder or a beet powder, or a combination thereof,
   preferably wherein the composition comprising the fungal biomass comprises mycelium bound to the particles of the powder dispersed in the growth medium, wherein preferably the growing mycelium traps the particles of the powder dispersed in the growth medium,
   preferably wherein the particles of the powder bound to the mycelium cannot be separated from the mycelium, preferably by washing, without disrupting the mycelium structure, preferably without disrupting the fungal cells.
6. The method of paragraph 4 or 5, wherein the particles of the powder bound to the mycelium constitute up to 25% w/w of the composition comprising the fungal biomass
   and/or
   wherein step (d) is performed before the commencement of step (c).
7. The method of any one of paragraphs 1 to 3, wherein the at least one additive that gives rise to the colour of the composition comprises a colourant that is assimilated by the at least one fungal strain, preferably wherein the assimilation of the colourant by the at least one fungal strain is dependent on the oxygen availability to the at least one fungal strain,
   preferably wherein step (e) is performed for not more than 72 hours, preferably not more than 48 hours.
8. The method of any one of paragraphs 6 or 7, wherein the colourant is a terpene compound, preferably wherein the colourant is astaxanthin or a derivative thereof.
9. The method of any one of paragraphs 1 to 3, wherein the at least one additive that gives rise to the colour of the composition comprises a coloured microorganism, preferably selected from red algae, green algae, brown algae and cyanobacteria,
   preferably wherein the composition comprising a fungal biomass further comprises a biomass of a coloured microorganism, preferably selected from red algae, green algae, brown algae and cyanobacteria.
10. The method of any one of paragraphs 1 to 9, wherein the supplementing in step (d) is done in the lag phase, in the acceleration phase, in the exponential phase, in the deceleration phase, or in the stationary phase of the biomass growth,
    preferably wherein the supplementing in step (d) is done in the deceleration phase or in the exponential phase of the biomass growth, more preferably wherein the supplementing in step (d) is done in the deceleration phase of the biomass growth,
    or preferably wherein the supplementing in step (d) is done in the lag phase.
11. The method of any one of paragraphs 1 to 10, wherein the supplementing in step (d) is done in the deceleration phase.
12. The method of any one of paragraphs 1 to 10, wherein the supplementing in step (d) is done in the exponential phase, preferably wherein the cultivation is performed as submerged fermentation performed as a continuous process.

13. The method of any one of paragraphs 1 to 12, further comprising the step of recovering a supernatant in step (f).
14. A composition obtainable according to the method of any one of paragraphs 1 to 13.
15. A food product comprising the composition of paragraph 14.
16. Use of the composition of paragraph 14 in the production of a food product.
17. A supernatant obtainable according to paragraph 13.
18. Use of the supernatant of paragraph 17 in the production of a food product.

The invention claimed is:
1. A method for the production of a composition comprising an edible fungal mycelium biomass, characterized in that said composition has a stable and homogenous colour, the method comprising the steps of:
  (a) providing a growth medium;
  (b) providing at least one edible fungal strain that produces mycelium;
  (c) cultivating the at least one edible fungal strain in the growth medium until deceleration phase is reached;
  (d) supplementing the growth medium with at least one colourant, wherein the supplementing is done in the deceleration phase;
  (e) further cultivating the at least one fungal strain in the growth medium supplemented with the at least one colourant; and
  (f) harvesting from the growth medium the composition comprising the edible fungal mycelium biomass, characterized in that said composition has the stable and homogenous colour
  due to the at least one colourant supplemented in step (d), wherein supplementing the at least one colourant in the deceleration phase results in a more stable and homogenous colouration of the composition relative to supplementing the at least one colourant at a time point other than the deceleration phase.
2. The method of claim 1, wherein the at least one fungal strain is selected from the group consisting of Peziomycetes, Agaricomycetes, and Sordariomycetes.
3. The method of claim 1, wherein the at least one fungal strain is selected from the group consisting of Pezizales, Boletales, Cantharellales, Agaricales, Polyporales, Russulales, Auriculariales, Sordoriales, and Hypocreales.
4. The method of claim 1, wherein the at least one fungal strain is selected from the group consisting of Morchellaceae, Tuberaceae, Pleurotaceae, Agaricaceae, Marasmiaceae, Cantharellaceae, Hydnaceae, Boletaceae, Meripilaceae, Polyporaceae, Strophariaceae, Lyophyllaceae, Tricholomataceae, Omphalotaceae, Physalacriaceae, Schizophyllaceae, Sclerodermataceae, Ganodermataceae, Sparassidaceae, Hericiaceae, Bondarzewiaceae, Cordycipitaceae, Auriculariaceae, Sordoriaceae, Nectriaceae and Fistulinaceae.
5. The method of claim 1, wherein the at least one fungal strain is selected from the group consisting of *Pleurotus pulmonarius, Pleurotus florida, Pleurotus citrinopileatus, Pleurotus salmoneostramineus, Morchella esculenta, Morchella angusticeps, Morchella deliciosa*, and *Morchella rufobrunnea*.
6. The method of claim 1, wherein the at least one fungal strain is *P. pulmonarius* or *Morchella rufobrunnea*.
7. The method of claim 1, wherein the growth medium further comprises vitamin B12 and/or omega-3 fatty acid(s).
8. The method of claim 1, wherein the at least one colourant comprises a powder, wherein optionally said powder forms dispersed phase when being supplemented to the growth medium in step (d).
9. The method of claim 8, wherein the powder is a cocoa powder, a duckweed powder, a spirulina powder, a paprika powder, a turmeric powder, a heme powder or a beet powder, or a combination thereof.
10. The method of claim 8, wherein a homogeneous colouration of the composition is achieved upon supplementing the powder to the growth medium in step (d).
11. The method of claim 1, wherein the at least one colourant is assimilated by the at least one fungal strain.
12. The method of claim 11, wherein the assimilation of the colourant by the at least one fungal strain is dependent on the oxygen availability to the at least one fungal strain.
13. The method of claim 11, wherein step (e) is performed for not more than 72 hours, optionally not more than 48 hours.
14. The method of claim 11, wherein the colourant is a terpene compound, optionally a carotenoid.
15. The method of claim 11, wherein the colourant is selected from the group consisting of xantophyll, carotene and chlorophyll.
16. The method of claim 14, wherein the colourant is astaxanthin or a derivative thereof.
17. The method of claim 1, wherein the colourant is selected from the group consisting of carotenoids, melanins, flavins, phenazines, quinones, monascins, violacein, indigo, anthraquinones, naphthaquinones, dihydroxy naphthalene melanin, flavin, monascorubamin, lycopene, ankaflavin, chrysophanol, cynodontin, helminthosporin, tritisporin, erythroglaucin, riboflavin, rubropunctatin; and pigments sourced from microbes such as, *Monascus* sp., *Xanthophyllomyces dendrorhous, Penicillium oxalicum, Ashbya gossypii, Blakeslea trispora, Erwinia uredovora, Rhodotorula mucilaginosa*, and *Fusarium sporotrichioides*.
18. The method of claim 1, wherein the at least one colourant is provided by a coloured microorganism added to the growth medium in the deceleration phase.
19. The method of claim 18, wherein the coloured microorganism comprises a fungus, optionally *Rhodotorula* fungus.
20. The method of claim 18, wherein the coloured microorganism is a microorganism selected from the group consisting of red algae, green algae, brown algae, and cyanobacteria.
21. The method of claim 18, wherein the coloured microorganism is a $CO_2$-fixing microbe, optionally wherein the $CO_2$-fixing microbe uses $CO_2$ produced by cultivating the at least one fungal strain in step c) or e) for its growth.
22. The method of claim 1, wherein the at least one colourant comprises a lignocellulosic liquid extract.
23. The method of claim 22, wherein the lignocellulosic liquid extract is selected from the group consisting of extracts of spent grain, cereal brans, wheat brans, cocoa, and coffee.
24. The method of claim 22, wherein the lignocellulosic liquid extract is extract of wheat brans and/or spent grain.
25. The method of claim 1, further comprising a step of recovering a supernatant in step (f).
26. A composition comprising an edible fungal mycelium biomass, wherein the composition is obtained according to a method comprising the steps of:
  (a) providing a growth medium;
  (b) providing at least one edible fungal strain that produces a mycelium;

(c) cultivating the at least one edible fungal strain in the growth medium until deceleration phase is reached;

(d) supplementing the growth medium with at least one colourant, wherein the supplementing is done in the deceleration phase;

(e) further cultivating the at least one fungal strain in the growth medium supplemented with the at least one colourant; and (f) harvesting from the growth medium the composition comprising the edible fungal mycelium biomass, characterized in that said composition has a stable and homogenous colour due to the at least one colourant supplemented in step (d), wherein supplementing the at least one colourant in the deceleration phase results in a more stable and homogenous colouration of the composition relative to supplementing the at least one colourant at a time point other than the deceleration phase; and optionally wherein the composition comprises:
at least 15 mg or 30 mg of the at least one colourant per 100 g of the fungal mycelium biomass, and/or
at least 0.01-5 wt. %, 0.1-5 wt. %, 0.1-2.5 wt. %, 0.1-1 wt. %, or 0.1-0.5 wt. % of the at least one colourant.

27. A food product comprising the composition of claim 26, optionally wherein the food product comprises an additive selected from preservatives, antioxidants and acidity regulators, thickeners, stabilisers and emulsifiers, pH regulators and anti-caking agents, flavor enhancers, improving agents, stabilizers, thickening agents, colours, and/or glazing agents and sweeteners, or wherein the food product is a beverage, optionally a Kombucha, or wherein the food product is an edible meat substitute product, an edible dairy substitute product or an edible fish analogue or seafood product.

28. A supernatant, obtained according to a method comprising the steps of:
(a) providing a growth medium;
(b) providing at least one edible fungal strain that produces a mycelium;
(c) cultivating the at least one edible fungal strain in the growth medium until deceleration phase is reached;
(d) supplementing the growth medium with at least one colourant, wherein the supplementing is done in the deceleration phase;
(e) further cultivating the at least one fungal strain in the growth medium supplemented with the at least one colourant; and
(f) harvesting from the growth medium the composition comprising the edible fungal mycelium biomass, characterized in that said composition has a stable and homogenous colour due to the at least one colourant supplemented in step (d); and
(g) recovering the supernatant from the composition harvested in step (f), wherein supplementing the at least one colourant in the deceleration phase results in a more stable and homogenous colouration of the composition relative to supplementing the at least one colourant at a time point other than the deceleration phase, and optionally wherein the supernatant comprises at least 0.1 wt. % of filamentous fungi.

29. The method of claim 1, wherein the cultivating step (c) is performed in a batch or fed-batch fermentation.

* * * * *